(12) United States Patent
Shenoy

(10) Patent No.: US 10,349,980 B2
(45) Date of Patent: Jul. 16, 2019

(54) METHOD AND APPARATUS FOR ALTERING BIOMECHANICS OF THE SHOULDER

(71) Applicant: Cotera, Inc., Menlo Park, CA (US)

(72) Inventor: Vivek Shenoy, Redwood City, CA (US)

(73) Assignee: The Foundry, LLC, Menlo Park, CA (US)

( * ) Notice: Subject to any disclaimer, the term of this patent is extended or adjusted under 35 U.S.C. 154(b) by 254 days.

(21) Appl. No.: 15/295,677

(22) Filed: Oct. 17, 2016

(65) Prior Publication Data

US 2017/0027708 A1 Feb. 2, 2017

Related U.S. Application Data

(63) Continuation-in-part of application No. 13/002,829, filed on Jan. 6, 2011, now Pat. No. 9,795,410, and a continuation-in-part of application No. 15/017,098, filed on Feb. 5, 2016, now Pat. No. 9,931,136, which is a continuation of application No. 13/843,128, filed on Mar. 15, 2013, now Pat. No. 9,278,004, and a
(Continued)

(51) Int. Cl.
*A61F 2/40* (2006.01)
*A61B 17/56* (2006.01)
*A61F 2/30* (2006.01)

(52) U.S. Cl.
CPC .... *A61B 17/56* (2013.01); *A61F 2002/30688* (2013.01)

(58) Field of Classification Search
CPC . A61B 17/56; A61B 17/562; A61B 2017/564; A61B 5/0555; A61B 5/1121; A61B 5/4528; A61B 6/0485
See application file for complete search history.

(56) References Cited

U.S. PATENT DOCUMENTS

| 2,632,440 A | 3/1953 | Hauser |
| 2,877,033 A | 3/1959 | Koetke |
| 3,242,922 A | 3/1966 | Thomas |

(Continued)

FOREIGN PATENT DOCUMENTS

| CA | 1205602 | 6/1986 |
| CN | 2788765 | 6/2006 |

(Continued)

OTHER PUBLICATIONS

Office Action dated Oct. 2, 2017, in connection with U.S. Appl. No. 15/295,560, filed Oct. 17, 2016.
(Continued)

*Primary Examiner* — Ann Schillinger
(74) *Attorney, Agent, or Firm* — Downs Rachlin Martin PLLC

(57) ABSTRACT

Selectively placed implants are specifically configured and dimensioned to address pathologies of the shoulder joint arising from improper force distribution. By using appropriately sized and positioned implants as described herein, displacement of targeted connective and muscle tissues acting on the shoulder is accomplished in order to realign force vectors and/or alter moment arms loading the joint to achieve therapeutic effects without cutting bone and with minimal cutting of the connective tissues.

14 Claims, 28 Drawing Sheets

Related U.S. Application Data continuation-in-part of application No. 12/870,462, filed on Aug. 27, 2010, now Pat. No. 8,597,362.

(60) Provisional application No. 62/242,099, filed on Oct. 15, 2015, provisional application No. 61/288,692, filed on Dec. 21, 2009, provisional application No. 61/620,756, filed on Apr. 5, 2012, provisional application No. 61/695,406, filed on Aug. 31, 2012, provisional application No. 61/237,518, filed on Aug. 27, 2009.

(56) References Cited

U.S. PATENT DOCUMENTS

| | | |
|---|---|---|
| 3,648,294 A | 3/1972 | Shahrestani |
| 3,681,786 A | 8/1972 | Lynch |
| 3,779,654 A | 12/1973 | Horne |
| 3,872,519 A | 3/1975 | Giannestras et al. |
| 3,875,594 A | 4/1975 | Lynch |
| 3,879,767 A | 4/1975 | Stubstad |
| 3,886,599 A | 6/1975 | Schlien |
| 3,889,300 A | 6/1975 | Smith |
| 3,902,482 A | 9/1975 | Taylor |
| 3,964,106 A | 6/1976 | Hutter, Jr. et al. |
| 3,985,127 A | 10/1976 | Volkov et al. |
| 3,988,783 A | 11/1976 | Treace |
| 4,007,495 A | 2/1977 | Frazier |
| 4,041,550 A | 8/1977 | Frazier |
| 4,052,753 A | 10/1977 | Dedo |
| 4,054,955 A | 10/1977 | Seppo |
| 4,069,518 A | 1/1978 | Groth, Jr. et al. |
| 4,156,944 A | 6/1979 | Schreiber et al. |
| 4,158,894 A | 6/1979 | Worrell |
| 4,164,793 A | 8/1979 | Swanson |
| 4,187,841 A | 2/1980 | Knutson |
| 4,246,660 A | 1/1981 | Wevers |
| 4,285,070 A | 8/1981 | Averill |
| 4,308,863 A | 1/1982 | Fischer |
| 4,353,361 A | 10/1982 | Foster |
| 4,367,562 A | 1/1983 | Gauthier |
| 4,470,158 A | 9/1984 | Pappas et al. |
| 4,501,266 A | 2/1985 | McDaniel |
| 4,570,625 A | 2/1986 | Harris |
| 4,576,158 A | 3/1986 | Boland |
| 4,621,627 A | 11/1986 | DeBastiani et al. |
| 4,637,382 A | 1/1987 | Walker |
| 4,642,122 A | 2/1987 | Steffee |
| 4,696,293 A | 9/1987 | Ciullo |
| 4,759,765 A | 7/1988 | Van Kampen |
| 4,759,766 A | 7/1988 | Buettner-Janz et al. |
| 4,776,851 A | 10/1988 | Bruchman et al. |
| 4,778,472 A | 10/1988 | Homsy et al. |
| 4,846,842 A | 7/1989 | Connolly et al. |
| 4,863,471 A | 9/1989 | Mansat |
| 4,871,367 A | 10/1989 | Christensen et al. |
| 4,873,967 A | 10/1989 | Sutherland |
| 4,883,486 A | 11/1989 | Kapadia et al. |
| 4,904,261 A | 2/1990 | Dove et al. |
| 4,919,672 A | 4/1990 | Millar et al. |
| 4,923,471 A | 5/1990 | Morgan |
| 4,942,875 A | 7/1990 | Hlavacek et al. |
| 4,955,915 A | 9/1990 | Swanson |
| 4,959,065 A | 9/1990 | Arnett et al. |
| 4,988,349 A | 1/1991 | Pennig |
| 4,988,350 A | 1/1991 | Herzberg |
| 5,002,574 A | 3/1991 | May et al. |
| 5,011,497 A | 4/1991 | Persson et al. |
| 5,019,077 A | 5/1991 | DeBastiani et al. |
| 5,019,104 A | 5/1991 | Whiteside et al. |
| 5,026,372 A | 6/1991 | Sturtzkopf et al. |
| 5,035,700 A | 7/1991 | Kenna |
| 5,041,112 A | 8/1991 | Mingozzi et al. |
| 5,100,403 A | 3/1992 | Hotchkiss et al. |
| 5,103,811 A | 4/1992 | Crupi |
| 5,121,742 A | 6/1992 | Engen |
| 5,152,280 A | 10/1992 | Danieli |
| 5,152,790 A | 10/1992 | Rosenberg et al. |
| 5,197,966 A | 3/1993 | Sommerkamp |
| 5,197,986 A | 3/1993 | Mikhail |
| 5,231,977 A | 8/1993 | Graston |
| 5,258,032 A | 11/1993 | Bertin |
| 5,304,180 A | 4/1994 | Slocum |
| 5,314,481 A | 5/1994 | Bianco |
| 5,318,567 A | 6/1994 | Vichard |
| 5,326,364 A | 6/1994 | Clift, Jr. et al. |
| 5,352,190 A | 10/1994 | Fischer |
| 5,375,823 A | 12/1994 | Navas |
| 5,383,937 A | 1/1995 | Mikhail |
| 5,405,347 A | 4/1995 | Lee et al. |
| 5,415,661 A | 5/1995 | Holmes |
| 5,425,775 A | 6/1995 | Kovacevic et al. |
| 5,456,722 A | 10/1995 | McLeod et al. |
| 5,480,443 A | 1/1996 | Elias |
| 5,540,688 A | 7/1996 | Navas |
| 5,545,229 A | 8/1996 | Parsons et al. |
| 5,571,198 A | 11/1996 | Drucker et al. |
| 5,575,819 A | 11/1996 | Amis |
| 5,578,038 A | 11/1996 | Slocum |
| 5,580,353 A | 12/1996 | Mendes et al. |
| 5,601,553 A | 2/1997 | Trebling et al. |
| 5,624,440 A | 4/1997 | Huebner |
| 5,662,648 A | 9/1997 | Faccioli et al. |
| 5,662,650 A | 9/1997 | Bailey et al. |
| 5,676,667 A | 10/1997 | Hausman |
| 5,681,313 A | 10/1997 | Diez |
| 5,695,496 A | 12/1997 | Orsak et al. |
| 5,702,460 A | 12/1997 | Carls et al. |
| 5,702,465 A | 12/1997 | Burkinshaw |
| 5,702,467 A | 12/1997 | Gabriel et al. |
| 5,716,357 A | 2/1998 | Rogozinski |
| 5,733,287 A | 3/1998 | Tepic et al. |
| 5,749,872 A | 5/1998 | Kyle et al. |
| 5,766,251 A | 6/1998 | Koshino |
| 5,803,924 A | 9/1998 | Oni et al. |
| 5,824,106 A | 10/1998 | Fournol |
| 5,871,540 A | 2/1999 | Weissman et al. |
| 5,873,843 A | 2/1999 | Draper |
| 5,879,386 A | 3/1999 | Jore |
| 5,888,203 A | 3/1999 | Goldberg |
| 5,928,234 A | 7/1999 | Manspeizer |
| 5,944,757 A | 8/1999 | Grammont |
| 5,976,125 A | 11/1999 | Graham |
| 5,976,136 A | 11/1999 | Bailey et al. |
| 5,989,292 A | 11/1999 | van Loon |
| 6,036,691 A | 3/2000 | Richardson |
| 6,096,040 A | 8/2000 | Esser |
| 6,113,637 A | 9/2000 | Gill et al. |
| 6,132,468 A | 10/2000 | Mansmann |
| 6,139,550 A | 10/2000 | Michelson |
| 6,143,032 A | 11/2000 | Schafer et al. |
| 6,146,423 A | 11/2000 | Cohen et al. |
| 6,161,080 A | 12/2000 | Aouni-Ateshian et al. |
| 6,162,223 A | 12/2000 | Orsak et al. |
| 6,176,860 B1 | 1/2001 | Howard |
| 6,193,225 B1 | 2/2001 | Watanabe |
| 6,200,347 B1 | 3/2001 | Anderson et al. |
| D443,060 S | 5/2001 | Benirschke et al. |
| 6,245,110 B1 | 6/2001 | Grundei et al. |
| 6,264,696 B1 | 7/2001 | Reigner et al. |
| 6,277,124 B1 | 8/2001 | Haag |
| 6,280,474 B1 | 8/2001 | Cassidy et al. |
| 6,302,915 B1 | 10/2001 | Cooney, III et al. |
| 6,315,798 B1 | 11/2001 | Ashby et al. |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,368,326 B1 | 4/2002 | Dakin et al. |
| 6,371,985 B1 | 4/2002 | Goldberg |
| 6,409,729 B1 | 6/2002 | Martinelli et al. |
| 6,409,767 B1 | 6/2002 | Perice et al. |
| 6,468,314 B2 | 10/2002 | Schwartz et al. |
| 6,482,232 B1 | 11/2002 | Boucher et al. |
| 6,485,503 B2 | 11/2002 | Jacobs et al. |

(56) References Cited

U.S. PATENT DOCUMENTS

| | | |
|---|---|---|
| 6,494,914 B2 | 12/2002 | Brown et al. |
| 6,520,964 B2 | 2/2003 | Tallarida et al. |
| 6,527,733 B1 | 3/2003 | Ceriani et al. |
| 6,540,708 B1 | 4/2003 | Manspeizer |
| 6,572,653 B1 | 6/2003 | Simonson |
| 6,579,318 B2 | 6/2003 | Varga et al. |
| 6,589,248 B1 | 7/2003 | Hughes |
| 6,592,622 B1 | 7/2003 | Ferguson |
| 6,599,321 B2 | 7/2003 | Hyde, Jr. |
| 6,599,322 B1 | 7/2003 | Amrich et al. |
| 6,616,696 B1 | 9/2003 | Merchant |
| 6,620,332 B2 | 9/2003 | Amrich |
| 6,623,486 B1 | 9/2003 | Weaver et al. |
| 6,626,945 B2 | 9/2003 | Simon et al. |
| 6,632,247 B2 | 10/2003 | Boyer, II et al. |
| 6,652,529 B2 | 11/2003 | Swanson |
| 6,663,631 B2 | 12/2003 | Kuntz |
| 6,679,914 B1 | 1/2004 | Gabbay |
| 6,692,497 B1 | 2/2004 | Tormala et al. |
| 6,692,498 B1 | 2/2004 | Niiranen et al. |
| 6,702,821 B2 | 3/2004 | Bonutti |
| 6,709,460 B2 | 3/2004 | Merchant |
| 6,712,856 B1 | 3/2004 | Carignan et al. |
| 6,719,794 B2 | 4/2004 | Gerber |
| 6,752,831 B2 | 6/2004 | Sybert et al. |
| 6,770,078 B2 | 8/2004 | Bonutti |
| 6,800,094 B2 | 10/2004 | Burkinshaw |
| 6,814,757 B2 | 11/2004 | Kopylov et al. |
| 6,824,567 B2 | 11/2004 | Tornier et al. |
| 6,852,125 B2 | 2/2005 | Simon et al. |
| 6,852,330 B2 | 2/2005 | Bowman et al. |
| 6,854,330 B2 | 2/2005 | Potter |
| 6,855,150 B1 | 2/2005 | Linchan |
| 6,866,684 B2 | 3/2005 | Fell et al. |
| 6,884,242 B2 | 4/2005 | LeHuec et al. |
| 6,890,358 B2 | 5/2005 | Ball et al. |
| 6,893,463 B2 | 5/2005 | Fell et al. |
| 6,896,702 B2 | 5/2005 | Collazo |
| 6,905,513 B1 | 6/2005 | Metzger |
| 6,911,044 B2 | 6/2005 | Fell et al. |
| 6,916,341 B2 | 7/2005 | Rolston |
| 6,926,739 B1 | 8/2005 | O'Connor et al. |
| 6,966,910 B2 | 11/2005 | Ritland |
| 6,966,928 B2 | 11/2005 | Fell et al. |
| 6,972,020 B1 | 12/2005 | Grayson et al. |
| 6,974,480 B2 | 12/2005 | Messerli et al. |
| 6,994,730 B2 | 2/2006 | Posner |
| 6,997,940 B2 | 2/2006 | Bonutti |
| 7,004,971 B2 | 2/2006 | Serhan et al. |
| 7,008,452 B2 | 3/2006 | Hawkins |
| 7,011,687 B2 | 3/2006 | Deffenbaugh et al. |
| 7,018,418 B2 | 3/2006 | Amrich et al. |
| 7,025,790 B2 | 4/2006 | Parks et al. |
| 7,029,475 B2 | 4/2006 | Pajabi |
| 7,060,073 B2 | 6/2006 | Frey et al. |
| 7,105,025 B2 | 9/2006 | Castro et al. |
| 7,105,027 B2 | 9/2006 | Lipman et al. |
| 7,124,762 B2 | 10/2006 | Carter et al. |
| 7,128,744 B2 | 10/2006 | Weaver et al. |
| 7,141,073 B2 | 11/2006 | May et al. |
| 7,160,333 B2 | 1/2007 | Plouhar et al. |
| 7,163,563 B2 | 1/2007 | Schwartz et al. |
| 7,182,787 B2 | 2/2007 | Hassler et al. |
| 7,188,626 B2 | 3/2007 | Foley et al. |
| 7,201,728 B2 | 4/2007 | Sterling |
| 7,223,292 B2 | 5/2007 | Messerli et al. |
| 7,226,482 B2 | 6/2007 | Messerli et al. |
| 7,226,483 B2 | 6/2007 | Gerber et al. |
| 7,235,077 B1 | 6/2007 | Wang et al. |
| 7,235,102 B2 | 6/2007 | Ferree et al. |
| 7,238,203 B2 | 7/2007 | Bagga et al. |
| 7,241,298 B2 | 7/2007 | Nemec et al. |
| 7,247,157 B2 | 7/2007 | Prager et al. |
| 7,252,670 B2 | 8/2007 | Morrison et al. |
| 7,261,739 B2 | 8/2007 | Ralph et al. |
| 7,273,481 B2 | 9/2007 | Lombardo et al. |
| 7,276,070 B2 | 10/2007 | Muckter |
| 7,282,065 B2 | 10/2007 | Kirschman |
| 7,285,134 B2 | 10/2007 | Berry et al. |
| 7,288,094 B2 | 10/2007 | Lindemann et al. |
| 7,288,095 B2 | 10/2007 | Baynham et al. |
| 7,291,150 B2 | 11/2007 | Graf |
| 7,291,169 B2 | 11/2007 | Hodorek |
| 7,297,161 B2 | 11/2007 | Fell |
| 7,306,605 B2 | 12/2007 | Ross |
| 7,322,983 B2 | 1/2008 | Harris |
| 7,322,984 B2 | 1/2008 | Doubler et al. |
| 7,323,012 B1 | 1/2008 | Stone et al. |
| 7,341,589 B2 | 3/2008 | Weaver et al. |
| 7,341,590 B2 | 3/2008 | Ferree |
| 7,341,602 B2 | 3/2008 | Fell et al. |
| 7,361,196 B2 | 4/2008 | Fallin et al. |
| 7,476,225 B2 | 1/2009 | Cole |
| 7,479,160 B2 | 1/2009 | Branch et al. |
| 7,485,147 B2 | 2/2009 | Pappas et al. |
| 7,500,991 B2 | 3/2009 | Bartish, Jr. et al. |
| 7,534,270 B2 | 5/2009 | Ball |
| 7,544,210 B2 | 6/2009 | Schaefer et al. |
| 7,553,331 B2 | 6/2009 | Manspeizer |
| 7,572,291 B2 | 8/2009 | Gil et al. |
| 7,611,540 B2 | 11/2009 | Clifford et al. |
| 7,618,454 B2 | 11/2009 | Bentley et al. |
| 7,632,310 B2 | 12/2009 | Clifford et al. |
| 7,632,311 B2 | 12/2009 | Seedhom et al. |
| 7,637,953 B2 | 12/2009 | Branch et al. |
| 7,641,689 B2 | 1/2010 | Fell et al. |
| 7,655,029 B2 | 2/2010 | Niederberger et al. |
| 7,655,041 B2 | 2/2010 | Clifford et al. |
| 7,678,147 B2 | 3/2010 | Clifford et al. |
| 7,722,676 B2 | 5/2010 | Hanson et al. |
| 7,723,395 B2 | 5/2010 | Ringeisen et al. |
| 7,726,319 B1 | 6/2010 | Boyce |
| 7,744,638 B2 | 6/2010 | Orbay |
| 7,749,276 B2 | 7/2010 | Fitz |
| 7,758,651 B2 | 7/2010 | Chauhan et al. |
| 7,780,670 B2 | 8/2010 | Bonutti |
| 7,806,898 B2 | 10/2010 | Justin et al. |
| 7,819,918 B2 | 10/2010 | Malaviya et al. |
| 7,828,852 B2 | 11/2010 | Bonutti |
| 7,846,211 B2 | 12/2010 | Clifford et al. |
| 7,875,082 B2 | 1/2011 | Naidu |
| 7,879,105 B2 | 2/2011 | Schmieding et al. |
| 7,896,921 B2 | 3/2011 | Smith et al. |
| 7,896,923 B2 | 3/2011 | Blackwell et al. |
| 7,951,176 B2 | 5/2011 | Grady et al. |
| 7,959,675 B2 | 6/2011 | Gately |
| 7,967,863 B2 | 6/2011 | Frey et al. |
| 7,972,383 B2 | 7/2011 | Goldstein et al. |
| 7,993,402 B2 | 8/2011 | Sidler |
| 8,002,833 B2 | 8/2011 | Fabris Monterumici et al. |
| 8,002,837 B2 | 8/2011 | Stream et al. |
| 8,002,841 B2 | 8/2011 | Hasselman |
| 8,034,117 B2 | 10/2011 | Matsuzaki et al. |
| 8,043,375 B2 | 10/2011 | Strzepa et al. |
| 8,043,380 B1 | 10/2011 | Park et al. |
| 8,052,753 B2 | 11/2011 | Melvin |
| 8,052,755 B2 | 11/2011 | Naidu |
| 8,083,746 B2 | 12/2011 | Novak |
| 8,088,166 B2 | 1/2012 | Makower et al. |
| 8,088,168 B2 | 1/2012 | Hassler et al. |
| 8,092,530 B2 | 1/2012 | Strzepa et al. |
| 8,092,544 B2 | 1/2012 | Wright et al. |
| 8,100,967 B2 | 1/2012 | Makower et al. |
| 8,114,156 B2 | 2/2012 | Hatch |
| 8,123,805 B2 | 2/2012 | Makower et al. |
| 8,128,697 B2 | 3/2012 | Fell et al. |
| 8,128,704 B2 | 3/2012 | Brown et al. |
| 8,142,503 B2 | 3/2012 | Malone |
| 8,257,444 B2 | 9/2012 | Linares |
| 8,262,707 B2 | 9/2012 | Huebner et al. |
| 8,267,972 B1 | 9/2012 | Gehlert |
| 8,282,681 B2 | 10/2012 | McLeod |
| 8,292,955 B2 | 10/2012 | Robinson |
| 8,328,805 B2 | 12/2012 | Cole |

(56) References Cited

U.S. PATENT DOCUMENTS

| | | |
|---|---|---|
| 8,372,078 B2 | 2/2013 | Collazo |
| 8,382,807 B2 | 2/2013 | Austin et al. |
| 8,523,921 B2 | 9/2013 | Horan et al. |
| 8,523,948 B2 | 9/2013 | Slone et al. |
| 8,597,362 B2 | 12/2013 | Shenoy et al. |
| 8,771,363 B2 | 7/2014 | Grotz |
| 8,845,724 B2 | 9/2014 | Shenoy et al. |
| 8,986,311 B2 | 3/2015 | Boudreault |
| 9,114,016 B2 | 8/2015 | Shenoy |
| 9,216,091 B2 | 12/2015 | Hardy |
| 9,278,004 B2 | 3/2016 | Shenoy |
| 2001/0020143 A1 | 9/2001 | Stark et al. |
| 2001/0023371 A1 | 9/2001 | Bonutti |
| 2001/0037155 A1 | 11/2001 | Merchant |
| 2002/0013587 A1 | 1/2002 | Winquist et al. |
| 2002/0029045 A1 | 3/2002 | Bonutti |
| 2002/0029084 A1 | 3/2002 | Paul et al. |
| 2002/0052606 A1 | 5/2002 | Bonutti |
| 2002/0065560 A1 | 5/2002 | Varga et al. |
| 2002/0091447 A1 | 7/2002 | Shimp et al. |
| 2002/0095154 A1 | 7/2002 | Atkinson et al. |
| 2002/0107574 A1 | 8/2002 | Boehm et al. |
| 2002/0133230 A1 | 9/2002 | Repicci |
| 2002/0151978 A1 | 10/2002 | Zacouto et al. |
| 2002/0165550 A1 | 11/2002 | Frey et al. |
| 2003/0055500 A1 | 3/2003 | Fell et al. |
| 2003/0083751 A1 | 5/2003 | Tornier |
| 2003/0088315 A1 | 5/2003 | Supinski |
| 2003/0100950 A1 | 5/2003 | Moret |
| 2003/0109928 A1 | 6/2003 | Pasquet et al. |
| 2003/0120344 A1 | 6/2003 | Michelson |
| 2003/0120346 A1 | 6/2003 | Mercinek et al. |
| 2003/0125807 A1 | 7/2003 | Lambrecht et al. |
| 2003/0139813 A1 | 7/2003 | Messerli et al. |
| 2003/0204265 A1 | 10/2003 | Short et al. |
| 2003/0216809 A1 | 11/2003 | Ferguson |
| 2004/0054409 A1 | 3/2004 | Harris |
| 2004/0117020 A1 | 6/2004 | Frey et al. |
| 2004/0127990 A1 | 7/2004 | Bartish, Jr. et al. |
| 2004/0133278 A1 | 7/2004 | Marino et al. |
| 2004/0143336 A1 | 7/2004 | Burkinshaw |
| 2004/0143338 A1 | 7/2004 | Burkinshaw |
| 2004/0148026 A1 | 7/2004 | Bonutti |
| 2004/0167630 A1 | 8/2004 | Rolston |
| 2004/0172133 A1 | 9/2004 | Gerber et al. |
| 2004/0186585 A1 | 9/2004 | Feiwell |
| 2004/0215195 A1 | 10/2004 | Shipp et al. |
| 2004/0230303 A1 | 11/2004 | Gomes et al. |
| 2004/0230315 A1 | 11/2004 | Ek |
| 2004/0236428 A1 | 11/2004 | Burkinshaw et al. |
| 2004/0243240 A1 | 12/2004 | Beaurain et al. |
| 2004/0260302 A1 | 12/2004 | Manspeizer |
| 2004/0267179 A1 | 12/2004 | Leman |
| 2004/0267375 A1 | 12/2004 | Friedrichs |
| 2005/0004671 A1 | 1/2005 | Ross et al. |
| 2005/0027360 A1 | 2/2005 | Webb et al. |
| 2005/0033424 A1 | 2/2005 | Fell |
| 2005/0033426 A1 | 2/2005 | Ogilvie et al. |
| 2005/0043808 A1 | 2/2005 | Felt et al. |
| 2005/0049708 A1 | 3/2005 | Atkinson et al. |
| 2005/0049711 A1 | 3/2005 | Ball |
| 2005/0085815 A1 | 4/2005 | Harms et al. |
| 2005/0119664 A1 | 6/2005 | Carignan et al. |
| 2005/0119744 A1 | 6/2005 | Buskirk et al. |
| 2005/0137708 A1 | 6/2005 | Clark |
| 2005/0143822 A1 | 6/2005 | Paul |
| 2005/0143830 A1 | 6/2005 | Marcinek et al. |
| 2005/0154390 A1 | 7/2005 | Biedermann et al. |
| 2005/0192674 A1 | 9/2005 | Ferree |
| 2005/0222685 A1 | 10/2005 | Hayden et al. |
| 2005/0251080 A1 | 11/2005 | Hyde, Jr. |
| 2005/0261680 A1 | 11/2005 | Draper |
| 2005/0261767 A1 | 11/2005 | Anderson et al. |
| 2005/0267584 A1 | 12/2005 | Burdulis, Jr. et al. |
| 2005/0273114 A1 | 12/2005 | Novak |
| 2005/0288788 A1 | 12/2005 | Dougherty-Shah |
| 2006/0036321 A1 | 2/2006 | Henninger et al. |
| 2006/0064169 A1 | 3/2006 | Ferree |
| 2006/0074492 A1 | 4/2006 | Frey |
| 2006/0085069 A1 | 4/2006 | Kim |
| 2006/0100715 A1 | 5/2006 | De Villiers |
| 2006/0106460 A1 | 5/2006 | Messerli et al. |
| 2006/0122620 A1 | 6/2006 | Kim |
| 2006/0129243 A1 | 6/2006 | Wong et al. |
| 2006/0142858 A1 | 6/2006 | Colleran et al. |
| 2006/0149274 A1 | 7/2006 | Justin et al. |
| 2006/0161260 A1 | 7/2006 | Thomas et al. |
| 2006/0074423 A1 | 8/2006 | Alleyne |
| 2006/0178744 A1 | 8/2006 | de Villiers et al. |
| 2006/0235387 A1 | 10/2006 | Peterman |
| 2006/0276907 A1 | 12/2006 | Boyer, II et al. |
| 2007/0027547 A1 | 2/2007 | Rydell et al. |
| 2007/0043356 A1 | 2/2007 | Timm et al. |
| 2007/0106299 A1 | 5/2007 | Manspeizer |
| 2007/0129804 A1 | 6/2007 | Bentley et al. |
| 2007/0129809 A1 | 6/2007 | Meridew et al. |
| 2007/0173946 A1 | 6/2007 | Bonutti |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0198088 A1 | 8/2007 | Biedermann et al. |
| 2007/0198091 A1 | 8/2007 | Boyer et al. |
| 2007/0203581 A1 | 8/2007 | Vanaclocha |
| 2007/0208343 A1 | 9/2007 | Magerl et al. |
| 2007/0225820 A1 | 9/2007 | Thomas et al. |
| 2007/0233141 A1 | 10/2007 | Park et al. |
| 2007/0244483 A9 | 10/2007 | Winslow et al. |
| 2007/0244488 A1 | 10/2007 | Metzger et al. |
| 2007/0265708 A1 | 11/2007 | Brown et al. |
| 2007/0276491 A1 | 11/2007 | Ahrens |
| 2007/0288014 A1 | 12/2007 | Shadduck et al. |
| 2007/0293947 A1 | 12/2007 | Mansmann |
| 2007/0299528 A9 | 12/2007 | Lotke |
| 2008/0015591 A1 | 1/2008 | Castaneda et al. |
| 2008/0015592 A1 | 1/2008 | Long et al. |
| 2008/0015593 A1 | 1/2008 | Pfefferie et al. |
| 2008/0015603 A1 | 1/2008 | Collazo |
| 2008/0015604 A1 | 1/2008 | Collazo |
| 2008/0021566 A1 | 1/2008 | Peters et al. |
| 2008/0033552 A1 | 2/2008 | Lee et al. |
| 2008/0044449 A1 | 2/2008 | McKay |
| 2008/0071373 A1 | 3/2008 | Molz et al. |
| 2008/0071375 A1 | 3/2008 | Carver et al. |
| 2008/0091270 A1 | 4/2008 | Millet et al. |
| 2008/0097434 A1 | 4/2008 | Moumene et al. |
| 2008/0097441 A1 | 4/2008 | Hayes et al. |
| 2008/0097617 A1 | 4/2008 | Fellinger et al. |
| 2008/0132954 A1 | 6/2008 | Sekhon et al. |
| 2008/0140094 A1 | 6/2008 | Schwartz et al. |
| 2008/0140213 A1 | 6/2008 | Ammann et al. |
| 2008/0154311 A1 | 6/2008 | Staeubli |
| 2008/0154371 A1 | 6/2008 | Fell et al. |
| 2008/0154378 A1 | 6/2008 | Pelo |
| 2008/0161815 A1 | 7/2008 | Schoenefeld et al. |
| 2008/0161933 A1 | 7/2008 | Grotz et al. |
| 2008/0195099 A1 | 8/2008 | Minas |
| 2008/0200995 A1 | 8/2008 | Sidebotham |
| 2008/0208341 A1 | 8/2008 | McCormack |
| 2008/0208346 A1 | 8/2008 | Schwartz |
| 2008/0234686 A1 | 9/2008 | Beaurain et al. |
| 2008/0262549 A1 | 10/2008 | Bennett et al. |
| 2008/0262618 A1 | 10/2008 | Hermsen et al. |
| 2008/0275509 A1 | 11/2008 | Clifford et al. |
| 2008/0275552 A1 | 11/2008 | Makower et al. |
| 2008/0275555 A1 | 11/2008 | Makower et al. |
| 2008/0275556 A1 | 11/2008 | Makower et al. |
| 2008/0275557 A1 | 11/2008 | Makower et al. |
| 2008/0275558 A1 | 11/2008 | Clifford et al. |
| 2008/0275559 A1 | 11/2008 | Makower et al. |
| 2008/0275560 A1 | 11/2008 | Clifford et al. |
| 2008/0275561 A1 | 11/2008 | Clifford et al. |
| 2008/0275562 A1 | 11/2008 | Clifford et al. |
| 2008/0275563 A1 | 11/2008 | Makower et al. |
| 2008/0275564 A1 | 11/2008 | Makower et al. |

(56) References Cited

U.S. PATENT DOCUMENTS

| | | |
|---|---|---|
| 2008/0275565 A1 | 11/2008 | Makower et al. |
| 2008/0275567 A1 | 11/2008 | Makower et al. |
| 2008/0275571 A1 | 11/2008 | Clifford et al. |
| 2008/0281422 A1 | 11/2008 | Schmieding |
| 2008/0281425 A1 | 11/2008 | Thalgott et al. |
| 2009/0012615 A1 | 1/2009 | Fell |
| 2009/0014016 A1 | 1/2009 | Clifford et al. |
| 2009/0018656 A1 | 1/2009 | Clifford et al. |
| 2009/0018665 A1 | 1/2009 | Clifford et al. |
| 2009/0036893 A1 | 2/2009 | Kartalian et al. |
| 2009/0048683 A1 | 2/2009 | Morris et al. |
| 2009/0076605 A1 | 3/2009 | Linares |
| 2009/0082808 A1 | 3/2009 | Butler |
| 2009/0088763 A1 | 4/2009 | Aram et al. |
| 2009/0088846 A1 | 4/2009 | Myung et al. |
| 2009/0112268 A1 | 4/2009 | Cole |
| 2009/0118830 A1 | 5/2009 | Fell |
| 2009/0132047 A1 | 5/2009 | Mansmann |
| 2009/0164014 A1 | 6/2009 | Liljensten et al. |
| 2009/0182433 A1 | 7/2009 | Reiley et al. |
| 2009/0187252 A1 | 7/2009 | Howald |
| 2009/0198341 A1 | 8/2009 | Choi et al. |
| 2009/0210063 A1 | 8/2009 | Barrett |
| 2009/0226068 A1 | 9/2009 | Fitz et al. |
| 2009/0248026 A1 | 10/2009 | Draper |
| 2009/0259311 A1 | 10/2009 | Shterling et al. |
| 2009/0259312 A1 | 10/2009 | Shterling et al. |
| 2009/0306783 A1 | 12/2009 | Blum |
| 2009/0312807 A1 | 12/2009 | Boudreault et al. |
| 2009/0318924 A1 | 12/2009 | Helenbolt et al. |
| 2009/0318976 A1 | 12/2009 | Gabriel et al. |
| 2010/0023126 A1 | 1/2010 | Grotz |
| 2010/0023127 A1 | 1/2010 | Shohat |
| 2010/0049322 A1 | 2/2010 | McKay |
| 2010/0049325 A1 | 2/2010 | Biedermann et al. |
| 2010/0057216 A1 | 3/2010 | Gannoe et al. |
| 2010/0076564 A1 | 3/2010 | Schilling et al. |
| 2010/0106247 A1 | 4/2010 | Makower et al. |
| 2010/0106248 A1 | 4/2010 | Makower et al. |
| 2010/0114322 A1 | 5/2010 | Clifford et al. |
| 2010/0121355 A1 | 5/2010 | Gittings et al. |
| 2010/0121457 A1 | 5/2010 | Clifford et al. |
| 2010/0125266 A1 | 5/2010 | Deem et al. |
| 2010/0131068 A1 | 5/2010 | Brown et al. |
| 2010/0131069 A1 | 5/2010 | Halbrecht |
| 2010/0137996 A1 | 6/2010 | Clifford et al. |
| 2010/0145449 A1 | 6/2010 | Makower et al. |
| 2010/0161057 A1 | 6/2010 | Berry et al. |
| 2010/0168857 A1 | 7/2010 | Hatch |
| 2010/0198354 A1 | 8/2010 | Halbrecht |
| 2010/0204798 A1 | 8/2010 | Gerbec et al. |
| 2010/0262246 A1 | 10/2010 | Attia |
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2010/0305708 A1 | 12/2010 | Lang et al. |
| 2011/0004305 A1 | 1/2011 | Jansson et al. |
| 2011/0054627 A1 | 3/2011 | Bear |
| 2011/0060422 A1 | 3/2011 | Makower et al. |
| 2011/0093073 A1 | 4/2011 | Gatt et al. |
| 2011/0093079 A1 | 4/2011 | Slone et al. |
| 2011/0093080 A1 | 4/2011 | Slone et al. |
| 2011/0121457 A1 | 5/2011 | Clevenger et al. |
| 2011/0137415 A1 | 6/2011 | Clifford et al. |
| 2011/0172768 A1 | 7/2011 | Cragg et al. |
| 2011/0178603 A1 | 7/2011 | Long |
| 2011/0202138 A1 | 8/2011 | Shenoy et al. |
| 2011/0213466 A1 | 9/2011 | Shenoy et al. |
| 2011/0224734 A1 | 9/2011 | Schelling |
| 2011/0230919 A1 | 9/2011 | Alleyne |
| 2011/0238180 A1 | 9/2011 | Fritz et al. |
| 2011/0245928 A1 | 10/2011 | Landry et al. |
| 2011/0264216 A1 | 10/2011 | Makower et al. |
| 2011/0270393 A1 | 11/2011 | Marvel |
| 2011/0288643 A1 | 11/2011 | Linder-Ganz et al. |
| 2012/0022649 A1 | 1/2012 | Robinson et al. |
| 2012/0022655 A1 | 1/2012 | Clifford |
| 2012/0046754 A1 | 2/2012 | Clifford et al. |
| 2012/0053644 A1 | 3/2012 | Landry et al. |
| 2012/0065640 A1 | 3/2012 | Metzger et al. |
| 2012/0116522 A1 | 5/2012 | Makower et al. |
| 2012/0136449 A1 | 5/2012 | Makower et al. |
| 2012/0179273 A1 | 7/2012 | Clifford et al. |
| 2012/0197410 A1 | 8/2012 | Horan et al. |
| 2012/0221106 A1 | 8/2012 | Makower et al. |
| 2012/0271366 A1 | 10/2012 | Katrana et al. |
| 2012/0290088 A1 | 11/2012 | Amirouche et al. |
| 2013/0013066 A1 | 1/2013 | Landry et al. |
| 2013/0013067 A1 | 1/2013 | Landry et al. |
| 2013/0018479 A1 | 1/2013 | Grotz |
| 2013/0041416 A1 | 2/2013 | Regala et al. |
| 2013/0096629 A1 | 4/2013 | Rollinghoff et al. |
| 2013/0150977 A1 | 6/2013 | Gabriel et al. |
| 2013/0166036 A1 | 6/2013 | De Cortanze et al. |
| 2013/0190886 A1 | 7/2013 | Tepic et al. |
| 2013/0204378 A1 | 8/2013 | Slone et al. |
| 2013/0211521 A1 | 8/2013 | Shenoy et al. |
| 2013/0289728 A1 | 10/2013 | Makower et al. |
| 2013/0304208 A1 | 11/2013 | Clifford et al. |
| 2013/0325123 A1 | 12/2013 | Clifford et al. |
| 2013/0338783 A1 | 12/2013 | Slone et al. |
| 2014/0052266 A1 | 2/2014 | Slone et al. |
| 2014/0128974 A1 | 5/2014 | Bromer |
| 2014/0156004 A1 | 6/2014 | Shenoy et al. |
| 2014/0156005 A1 | 6/2014 | Shenoy et al. |
| 2014/0257292 A1 | 9/2014 | Embleton et al. |
| 2014/0343675 A1 | 11/2014 | Vanleeuwen |
| 2014/0371864 A1 | 12/2014 | Shohat |
| 2016/0213402 A1 | 7/2016 | Shenoy |
| 2016/0256286 A1* | 9/2016 | Morris .................. A61B 17/56 |
| 2017/0027708 A1 | 2/2017 | Shenoy |

FOREIGN PATENT DOCUMENTS

| | | |
|---|---|---|
| DE | 19855254 A1 | 6/2000 |
| EP | 0383419 A1 | 8/1990 |
| EP | 0953317 B1 | 4/2004 |
| EP | 1410769 A2 | 4/2004 |
| EP | 1770302 A1 | 4/2007 |
| EP | 1429675 B1 | 10/2007 |
| EP | 1682020 B1 | 10/2007 |
| EP | 1847228 A1 | 10/2007 |
| EP | 1847229 A2 | 10/2007 |
| EP | 1005290 B1 | 2/2008 |
| EP | 1468655 B1 | 5/2008 |
| EP | 2452641 A1 | 5/2012 |
| FR | 2926456 A1 | 7/2009 |
| GB | 1507953 | 4/1978 |
| GB | 2223406 | 4/1990 |
| GB | 2250919 | 10/1993 |
| JP | 59131348 | 7/1984 |
| JP | 7100159 | 4/1995 |
| JP | 2532346 B2 | 11/1996 |
| JP | 2000503865 | 4/2000 |
| JP | 2001145647 | 5/2001 |
| JP | 2003102744 | 4/2003 |
| JP | 2006280951 | 10/2006 |
| JP | 2007167318 | 7/2007 |
| JP | 2007167319 | 7/2007 |
| JP | 2007170969 | 7/2007 |
| JP | 2011519303 T | 7/2011 |
| NZ | 533300 | 2/2005 |
| RU | 2085148 | 7/1997 |
| RU | 2217105 C2 | 11/2003 |
| RU | 2241400 C2 | 12/2004 |
| SU | 578063 A1 | 10/1977 |
| SU | 578957 A1 | 11/1977 |
| SU | 624613 A1 | 9/1978 |
| SU | 640740 A1 | 1/1979 |
| SU | 704605 A1 | 12/1979 |
| SU | 719612 A1 | 3/1980 |
| SU | 741872 A1 | 6/1980 |
| SU | 1186204 | 10/1985 |
| SU | 1251889 | 8/1986 |

(56) References Cited

FOREIGN PATENT DOCUMENTS

| | | |
|---|---|---|
| SU | 1316666 A1 | 6/1987 |
| SU | 1588404 | 8/1990 |
| SU | 1699441 A1 | 12/1991 |
| SU | 1769868 A1 | 10/1992 |
| WO | 91/07137 | 5/1991 |
| WO | 94/06364 A1 | 3/1994 |
| WO | 96/19944 A1 | 7/1996 |
| WO | 2004019831 A2 | 3/2004 |
| WO | 2004024037 A2 | 3/2004 |
| WO | 2006045091 A2 | 4/2006 |
| WO | 2006049993 | 5/2006 |
| WO | 2006110578 A3 | 10/2006 |
| WO | 2007056645 A2 | 5/2007 |
| WO | 2007090009 A1 | 8/2007 |
| WO | 2007090015 A1 | 8/2007 |
| WO | 2007090017 A1 | 8/2007 |
| WO | 2007106962 A1 | 9/2007 |
| WO | 2007109132 A2 | 9/2007 |
| WO | 2007109140 A2 | 9/2007 |
| WO | 2007109417 A2 | 9/2007 |
| WO | 2007109436 A2 | 9/2007 |
| WO | 2007114769 A1 | 10/2007 |
| WO | 2007117571 A2 | 10/2007 |
| WO | 2008006098 A2 | 1/2008 |
| WO | 2009009618 A1 | 1/2009 |
| WO | 2009018365 A1 | 2/2009 |
| WO | 2011025959 A1 | 3/2011 |
| WO | 2012062908 A1 | 5/2012 |

OTHER PUBLICATIONS

Response to Office Action dated Mar. 2, 2018, in connection with U.S. Appl. No. 15/295,560, filed Oct. 17, 2016.
Final Office Action dated Jun. 14, 2018, in connection with U.S. Appl. No. 15/295,560, filed Oct. 17, 2016.
Lapinskaya, Valentina Spiridonovna, "Treatment of Diseases and Injuries of Hip Joint Using a Method of Distraction", Kuibyshev Medical Institute, 1990.
Larionov D. Yu, et al., "Medical Devices," Scientific and Technical Bimonthly Journal, May-Jun. 2008.
Lapinskaya, V.S., et al., "An Endoapparatus for Restoration of the Hip Joint," Writers Collective, 2008, UDK 615.472.03:616.728.2-089.28; pp. 8-12.
Tomita, Naohide, "Development of Treatment Devices for Cartilage Regeneration", BME vol. 16, No. 2.
Lentsner, A.A., et al., "Device for Functional Relief of Hip Joint in Cotyloid Cavity Fracture Cases", Ortop Travmatol Protez. Apr. 1990 (4) 44-6.
Aldegheri, Roberto, M.C., et al.; "Articulated Distraction of the Hip Conservative Surgery for Arthritis in Young Patients," Clinical Orthopaedics and Related Research, No. 301, pp. 94-101.
Andriacchi, Thomas P., Ph.D. et al.; "Methods for Evaluating the Progression of Osteoarthritis"; Journal of Rehabilitation Research and Development, vol. 37, No. 2., Mar./Apr. 2000, pp. 163-170.
Arendt, Elizabeth, M.D.; "Anatomy and Malalignment of the Patellofemoral Joint—Its Relation to Patellofemoral Arthrosis"; Clinical Orthopaedics and Related Research; 2005, No. 436, pp. 71-75.
Benzel, Edward; "Qualitative Attributes of Spinal Implants"; in: Biomechanics of Spine Stabilization, 1995, pp. 137-150.
Buckwalter, Joseph A.; "Joint Distraction for Osteoarthritis"; The Lancet, Department of Orthopaedic Surgery, University of Iowa Hospitals and Clinics, vol. 347, Feb. 3, 1996, pp. 279-280.
Coathup, M.J. et al.; "Osseo-mechanical induction of extra-cortical plates with reference to their surface properties and gemoetric designs", Elsevier, Biomaterials 20 (1999) pp. 793-800.
Deie, Masataka, M.D. et al.; "A New Articulated Distraction Arthroplasty Device for Treatment of the Osteoarthritic Knee Joint: A Preliminary Report"; Arthroscopy: The Journal of Arthroscopic and Related Surgery; vol. 23, No. 8 Aug. 2007: pp. 833-838.
Dienst, M. et al.; "Dynamic External Fixation for Distal Radius Fractures"; Clinical Orthopaedics and Related Research, 1997, vol. 338, pp. 160-171.
Gunther, Klaus-Peter, M.D.; "Surgical Approaches for Osteoarthritis"; Best Practice & Research Clinical Rheumatology, vol. 15, No. 4, 2001, pp. 627-643.
Hall, J. et al.; "Use of a Hinged External Fixator for Elbow instability after Severe Distal Humeral Fracture"; Journal of Orthopaedic Trauma, 2000, vol. 14, No. 6, pp. 442-448.
Klein, D. et al.; "Percutaneous Treatment of Carnal, Metacarpal, and Phalangeal Injuries"; Clinical Orthopaedics and Related Research, 2000, vol. 375, pp. 116-125.
Krakauer J. et al.; "Hinged Device for Fractures involving the Proximal Interphalangeal Joint"; Clinical Orthopaedics and Related Research, 1996, vol. 327, pp. 29-37.
Leon, Heriberto Ojeda, M.D. et al.; "Minimally Invasive Selective Osteotomy of the Knee: A New Surgical Technique"; Arthroscopy: The Journal of Arthroscopic and Related Surgery, vol. 17, No. 5 May-Jun. 2001: pp. 510-516.
Madey, S. et al.; "Hinged External Fixation of the elbow: optimal axis alignment to minimize motion resistance"; Journal of Orthopaedic Trauma, 2000, vol. 14, No. 1, pp. 41-47.
Neel, Michael D., M.D. et al.; "Early Multicenter Experience With a Noninvasive Expandable Prosthesis"; Clinical Orthopaedics and Related Research, 2003, No. 415, pp. 72-81.
Neel, Michael D., M.D.; "Repiphysis—Limb Salvage System for the Skeletally Immature"; Wright Medical Technology, Reipiphysis Limb Salvage System, 2004, pp. 1-8.
Nockels, Russ P.; "Dynamic Stabilization in the Surgical Management of Painful Lumbar Spinal Disorders"; Spine, 2005, vol. 30, No. 16S, pp. S68-S72.
ORTHOFIX; "Xcaliber Articulated Ankle"; advertising brochure, May 2004.
ORTHOFIX; "Gentle Limb Deformity Correction"; website pages, http://www.eight-plate.com/, 2008.
Perry, Clayton R. et al.; "Patellar Fixation Protected with a Load-Sharing Cable: A Mechanical and Clinical Study"; Journal of Orthopaedic Trauma, 1988, vol. 2, No. 3, pp. 234-240.
Pilliar et al., "Bone Ingrowth and Stress Shielding with a Porous Surface Coated Fracture Fixation Plate," Journal of Biomedical Materials Research, vol. 13, (1979), pp. 799-810.
Repicci, John A., M.D. et al. "Minimally Invasive Unicondylar Knee Arthroplasty for the Treatment of Unicompartmental Osteoarthritis: an outpatient arthritic bypass procedure"; Orthopedic Clinics of North America, 35 (2004), pp. 201-216.
Sharma, Leena et al. "The Mechanism of the Effect of Obesity in Knee Osteoarthritis—The Mediating Role of Malalignment"; Arthritis & Rheumatism, vol. 43, No. 3, Mar. 2000, pp. 568-575.
Sommerkamp, G. et al.; "Dynamic External Fixation of Unstable Fractures of the Distal Part of the Radius"; The Journal of Bone and Joint Surgery; Aug. 1994, vol. 76-A, No. 8, pp. 1149-1161.
Tencer, Allan F. et al. "Fixation of the Patella (Chap. 9.3)"; in: Biomechanics in Orthopedic Trauma Bone Fracture and Fixation, 1994.
Thakur, A.J.; "Tension Band Wiring"; in; The Elements of Fracture Fixation, 1997, pp. 126-146.
Uchikura, C. et al.; "Comparative Study of Nonbridging and Bridging External Fixators from Unstable Distal Radius fractures"; Journal of Orthopaedic Science, 2004, vol. 9, No. 6, pp. 560-565.
Van Der Esch, M. et al.; "Structural Joint Changes, Malalignment, and Laxity in Osteoarthritis of the knee"; Scand J Rheumatol 2005; 34: pp. 298-301.
Weisstein, Jason S., M.D. et al.; "Oncologic Approaches to Pediatric Limb Preservation"; Journal of the American Academy of Orthopaedic Surgeons; vol. 13, No. 8, Dec. 2005, pp. 544-554.
Wilke, Hans-Joachim et al.; "Biomechanical Evaluation of a New Total Posterior-Element Replacement System"; Spine, 2006, vol. 31, No. 24, pp. 2790-2796.
Wilkins, Ross M., M.D. et al. "The Phenix Expandable Prosthesis"; Clinical Orthopaedics and Related Research, No. 382, pp. 51-58.
Yamamoto, Ei et al.; "Effects of Stress Shielding on the Transverse Mechanical Properties of Rabbit Patellar Tendons"; Journal of Biomechanical Engineering, 2000, vol. 122, pp. 608-614.

(56) References Cited

OTHER PUBLICATIONS

Nagai, et al., "B109 Mobility Evaluation of Hip-Joint Nonweight-Bearing Device," The Japan Society of Mechanical Engineers No. 02-26.
European Search Report dated Aug. 7, 2014, issued in connection with related EP14164658.
Extended Search Report dated Aug. 26, 2014, issued in connection with related EP14164658.
Non-Final Rejection Office Action dated Aug. 27, 2014, in connection with related U.S. Appl. No. 14/175,813, filed Feb. 7, 2014.
Notice of Allowance dated Aug. 4, 2014 in connection with related U.S. Appl. No. 14/175,829, filed Feb. 7, 2014, Vivek Shenoy.
Office Action dated Dec. 19, 2014, in connection with U.S. Appl. No. 13/843,128, filed Mar. 15, 2013.
Response to Final Office Action dated Apr. 1, 2013, in connection with related U.S. Appl. No. 13/002,829, filed Aug. 27, 2009.
Response to First Non-Final Office Action dated May 5, 2014, in connection with related U.S. Appl. No. 14/175,829, filed Feb. 7, 2014.
Response to Restriction Requirement dated Oct. 27, 2014, issued in connection with related U.S. Appl. No. 13/843,128, filed Mar. 15, 2013.
Restriction Requirement dated Aug. 25, 2014, issued in connection with related U.S. Appl. No. 13/843,128, filed Mar. 15, 2013.
Non-Final Office Action dated Apr. 11, 2014, in connection with related U.S. Appl. No. 14/175,829, filed Feb. 2, 2014, Vivek Shenoy.
Final Office Action dated Feb. 26, 2015, in connection with related U.S. Appl. No. 13/002,829, filed Jan. 6, 2011.
Response to Non-Final Office Action dated May 26, 2015, in connection with related U.S. Appl. No. 13/002,829, filed Jan. 6, 2011.
Response to Non-Final Office Action dated Apr. 20, 2015, in connection with related U.S. Appl. No. 13/843,128, filed Mar. 15, 2013.
Final Office Action dated Jun. 10, 2015, in connection with related U.S. Appl. No. 13/843,128, filed Mar. 15, 2013.
Partial International Search dated May 11, 2015, in connection with related PCT/US2015/019938, filed Mar. 11, 2015.
International Search Report and Written Opinion dated Jul. 3, 2015, in connection with related PCT/US2015/019938, fled Mar. 11, 2015.
Office Action dated Jul. 1, 2015, in connection with related U.S. Appl. No. 13/974,930, filed Aug. 23, 2013.
Restriction Requirement dated Jul. 23, 2015, in connection with related U.S. Appl. No. 14/642,121, filed Mar. 9, 2015.
Response to Final Office Action dated Aug. 10, 2015, in connection with related U.S. Appl. No. 13/843,128, filed Mar. 15, 2013.
Response to Restriction Requirement dated Sep. 23, 2015, in connection with related U.S. Appl. No. 14/642,121, filed Mar. 9, 2015.
Supplemental Response to Final Office Action dated Sep. 3, 2015, in connection with related U.S. Appl. No. 13/843,128, filed Mar. 15, 2013.
Final Office Action dated Sep. 15, 2015, in connection with related U.S. Appl. No. 13/002,829, filed Jan. 6, 2011.
Chow, S. P. et al., Fracture of the Tibial Tubercle in the Adolescent; British Editorial Society of Bone and Joint Surgery, vol. 72-B. No. 2, Mar. 1990.
Response to First Non-Final Office Action dated Nov. 2, 2015, in connection with U.S. Appl. No. 13/974,930, filed Aug. 23, 2013.
Non-Final Office Action dated Oct. 7, 2015, in connection with U.S. Appl. No. 14/642,121, filed Mar. 9, 2015.
Gumpel et al., An Objective Assessment of Synovitis of the Knee: Measurement of the Size of the Suprapatellar Pouch on Xeroradiography. Annals of the Rheumatic Diseases. 1980, (39): 359-366.
Response to First Non-Final Office Action dated Jan. 25, 2016, in connection with related U.S. Appl. No. 14/642,121, filed Mar. 9, 2015.

Office Action dated Feb. 26, 2016, in connection with related U.S. Appl. No. 13/974,930, filed Aug. 23, 2013.
Appellant's Brief dated Mar. 15, 2016, in connection with related U.S. Appl. No. 13/002,829, filed Jan. 6, 2011.
Lafaver, et al., "Tibial Tuberosity Advancement for Stabilization of the Canine Cranial Cruciate Ligament-Deficient Stifle Joint: Surgical Technique, Early Results, and Complications in 101 Dogs", Veterinary Surgery, 36:573-586, 2007.
Office Action dated May 5, 2016, in connection with U.S. Appl. No. 14/642,121, filed Mar. 9, 2015, Shenoy.
Examination Search Report dated Sep. 6, 2016, in connection with Canadian Application No. 2,771,332.
Response to Second Non-Final Office Action dated Oct. 5, 2016, in connection with U.S. Appl. No. 14/642,121, filed Mar. 9, 2015, Shenoy.
Notice of Allowance dated Jun. 21, 2016, in connection with U.S. Appl. No. 13/974,930, filed Aug. 23, 2013, Shenoy.
Restriction Requirement dated Jul. 22, 2015, in connection with related U.S. Appl. No. 14/644,792, filed Mar. 11, 2015.
Response to Restriction Requirement dated Sep. 11, 2015, in connection with related U.S. Appl. No. 14/644,792, filed Mar. 11, 2015.
Non-final Office Action dated Sep. 25, 2015, in connection with related U.S. Appl. No. 14/644,792, filed Mar. 11, 2015.
Office Action dated May 18, 2016, in connection with U.S. Appl. No. 14/644,792, filed Mar. 11, 2015, Shenoy.
Amendment and Response to Second Non-Final Office Action dated Sep. 19, 2016, in connection with U.S. Appl. No. 14/644,792, filed Mar. 11, 2015, Shenoy.
Office Action dated Oct. 6, 2016, in connection with U.S. Appl. No. 13/002,829, filed Jan. 6, 2011, Shenoy.
Response to Final Office Action dated Apr. 26, 2016, in connection with U.S. Appl. No. 13/974,930, filed Aug. 23, 2013.
Amendment and Response to First Non-Final Office Action dated Feb. 3, 2016, in connection with U.S. Appl. No. 14/644,792, filed Mar. 11, 2015, Shenoy.
Response to Final Office Action dated Apr. 26, 2016, in connection with U.S. Appl. No. 13/974,930, filed Aug. 23, 2013, Shenoy.
Notice of Allowance dated Feb. 3, 2015, in connection with related U.S. Appl. No. 14/175,813, filed Feb. 7, 2014.
Synthes, Inc., LCP Proximal Tibial Plate 3.5; Technique Guide; pp. 1-20; Jun. 2011.
Synthes TomoFix Osteotomy System Technique Guide: A comprehensive plating system for stable fixation of osteotomies around the knee. 38 pages.
LOQTEQ Anatomical Plating System Design Rationale. Locking Compression Technology by aap. aap Implantate AG. 11 pages.
Response to Election/Restriction dated Jul. 1, 2014 in connection with related U.S. Appl. No. 14/175,813, filed Feb. 7, 2014.
Arnoczky et al., Biomechanical Analysis of Forces Acting About the Canine Hip, American Journal Veterinary Research, vol. 42, Issue: 9, Sep. 1981, pp. 1581-1585.
Becker et al., Surgical Treatment of Isolated Patellofemoral Osteoarthritis, Clinical Orthopaedics and Related Research vol. 466, No. 2, Feb. 2008, pp. 443-449.
Cerejo et al., The Influence of Alignment on Risk of Knee Osteoarthritis Progression According to Baseline Stage of Disease, Arthritis & Rheumatism, vol. 46, No. 10, Oct. 2002, pp. 2632-2636.
Clifford et al., The KineSpring load absorber implant: Rationale, Design and Biomechanical Characterization, Journal of Medical Engineering & Technology, vol. 35, No. 1, Jan. 2011, pp. 65-71.
Delp et al., An Interactive Graphics-Based Model of the Lower Extremity to Study Orthopaedic Surgical Procedures, IEEE Transactions on Biomedical Engineering, vol. 37, No. 8, Aug. 1990, pp. 757-767.
Delp et al., Biomechanical Analysis of the Chiari Pelvic Osteotomy Preserving Hip Abductor Strength, Reprinted from Clinical Orthopaedics, vol. 25, May, 1990, pp. 189-198.
Free et al, Trochanteric Transfer in Total Hip Replacement: Effects on the Moment Arms and Force-Generating Capacities of the Hip Abductors, Journal of Orthopaedic Research, vol. 14, No. 2, 1996, pp. 245-250.

(56) References Cited

OTHER PUBLICATIONS

Jack Farr, M.D., Tibial Tubercle Osteotomy, Techniques in Knee Surgery, vol. 2, Issue 1, 2003, pp. 28-42.
Goetz et al., Hip Joint Contact Force in the Emu (Dromaius novaehollandiae) during Normal Level Walking, Journal of Biomechanics, 41(4), 2008, pp. 770-778.
Jacobsen et al., Hip dysplasia: a significant risk factor for the development of hip osteoarthritis. A cross-sectional survey, Rheumatology vol. 44 No. 2, 2005, pp. 211-218.
Jingushi et al., Transtrochanteric Valgus Osteotomy for the Treatment of Osteoarthritis of the Hip Secondary to Acetabular Dysplasia, The Journal of Bone & Joint Surgery [Br], vol. 84-B, No. 4, May 2002, pp. 535-539.
Kirkley et al., The Effect of Bracing on Varus Gonarthrosis, The Journal of Bone and Joint Surgery, vol. 81-A, No. 4, Apr. 1999, pp. 539-548.
Lafeber et al., Unloading Joints to Treat Osteoarthritis, including Joint Distraction, Current Opinion in Rheumatology 2006, 18, pp. 519-525.
Lloyd et al., An EMG-driven Musculoskeletal Model to Estimate Muscle Forces and Knee Joint Moments in Vivo, Journal of Biomechanics 36, 2003, pp. 765-776.
Lloyd et al., Strategies of Muscular Support of Varus Andvalgus Isometric Loads at the Human Knee, Journal of Biomechanics 34, 2001, pp. 1257-1267.
Maquet, P, Biomechanics of Hip Dysplasia, Acta Ortopaedica Belgica, vol. 65—Mar. 1999, pp. 302-314.
McWilliams et al., Mild Acetabular Dysplasia and Risk of Osteoarthritis of the hip: a case-control study, Annals of the Rheumatic Diseases, 2010; 69, pp. 1774-1778.
Merritt et al., Influence of Muscle-Tendon Wrapping on Calculations of Joint Reaction Forces in the Equine Distal Forelimb, Journal of Biomedicine and Biotechnology, vol. 2008, Article ID 165730, 9 pages.
Pedersen et al., A Model to Predict Canine Pelvic Limb Musuloskeletal Geometry, Acta Anat 1991; 140, pp. 139-145.
Pollo et al., Knee Bracing for Unicompartmental Osteoarthritis, Journal of the American Academy of Orthopaedic Surgeons, vol. 14, No. 1, Jan. 2006, pp. 5-11.
Pollo et al., Reduction of Medial Compartment Loads with Valgus Bracing of the Osteoarthritic Knee, The American Journal of Sports Medicine, vol. 30, No. 3, 2002, pp. 414-421.
Saleh et al., Operative Treatment of Patellofemoral Arthritis, The Journal of Bone & Joint Surgery, vol. 87-A, No. 3, Mar. 2005, pp. 659-671.
Sharma et al., The Role of Knee Alignment in Disease Progression and Functional Decline in Knee Osteoarthritis, JAMA, vol. 286, No. 2, Jul. 11, 2001, pp. 188-195.
Sims et al., Investigation of Hip Abductor Activation in Subjects with Clinical Unilateral Hip Osteoarthritis, Annals of the Rheumatic Diseases, 2002; 61: pp. 687-692.
Thorp et al., The biomechanical effects of focused muscle training on medial knee loads in OA of the knee: a pilot, proof of concept study, Journal of Musculoskeletal and Neuronal Interactions, 10(2): 2010, pp. 166-173.
Wenger et al., Early Surgical Correction of Residual Hip Dysplasia: The San Diego Children's Hospital Approach, Acta Orthopaedica Belgica, vol. 65, 1999, pp. 277-287.
Winby et al., Muscle and External Load Contribution to Knee Joint Contact Loads during Normal Gait, Journal of Biomechanics 42, 2009, pp. 2294-2300.
Response to Final Office Action dated Apr. 1, 2013, in connection with related U.S. Appl. No. 13/002,829 International filing date Aug. 27, 2010.
Amendment and Response to Final Office Action dated May 20, 2013, in connection with related U.S. Appl. No. 12/870,462, filed Aug. 27, 2010.
Advisory Action dated Apr. 23, 2013 in connection with related U.S. Appl. No. 13/002,829, filed Jan. 6, 2011.
Advisory Action dated Jun. 20, 2013 in connection with related U.S. Appl. No. 13/002,829, filed Jan. 6, 2011.
Tew, M et al.; Anteriorization of the quadriceps tendon. A biomechanical study on a new technique for unloading the patellofemoral joint. University of Tennessee College of Medicine; Poster No. 0848 • ORS 2012 Annual Meeting.
Miller, R.K, Goodfellow, J.W., Murray, D.W. and O'Connor, J.J., In vitro measurement of patellofemoral force after three types of knee replacement; The Journal of Bone & Joint Surgery (Br), vol. 80-B, No. 5, Sep. 1998; pp. 900-906.
Ganesh, V.K., et al., Biomechanics of bone-fracture fixation by stiffness-graded plates in comparison with stainless-steel plates, Biomedical Engineering Online, 2005, 4:46, 15 pgs.
Benli, Semih et al., Evaluation of bone plate with low-stiffness material in terms of stress distribution, Journal of Biomechanics, 41 (2008) 3229-3235.
Haase, Kristina et al., A Discussion on Plating Factors that Affect Stress Shielding Using Finite Element Analysis, Journal of Biomechanical Science and Engineering, vol. 5, No. 2, 2010, pp. 129.
Anatomic Locked Plating System Brochure, BIOMET® Orthopedics, Form BMET0002.0, REV 053112, pp. 1-16, Copyright 2012.
SPS Periarticular Plates Brochure, STRYKER® Trauma AG, Literature No. 982274, Lot B46404, pp. 1-8; Copyright 2004.
Zimmer® Periarticular Distal Femoral Locking Plate Surgical Technique, the Science of the Landscape, ZIMMER, 97-2347-044-00 Rev. 1 7.5 ML; pp. 1-20; Copyright 2005.
Hessmann et al., Compression Plate With or Without Lag Screw; AO Surgery Reference—Online reference in clinical life; Distal Tibia—Reduction & Fixation—Compression Plate; https://www2.aofoundation.org/wps/portal; pp. 1-9; Dec. 3, 2008.
LCP Locking Compression Plate—Ordering Information; SYNTHES®, 036.000.017, SE_042064 AD, 31080015; pp. 1-68; Copyright 2008.
Plates for 4.5 mm and 6.5 mm Screws; Raj Surgical Works; http://www.orthoindustries.com/plates-for-4-5-mm-and-6-5-mm-screws.html; pp. 1-8; printed Nov. 19, 2012.
Final (Rejection) Office Action dated Mar. 18, 2013, in connection with related U.S. Appl. No. 12/870,462, filed Aug. 27, 2010.
Final Office Action dated Jan. 31, 2013, in connection with related U.S. Appl. No. 13/002,829, filed Jan. 6, 2011.
PCT International Search Report and Written Opinion dated Jan. 9, 2014, for related application PCT/US2013/058877 filed Sep. 10, 2013 entitled "Method and Apparatus for Treating Canine Cruciate Ligament Disease," Vivek Shenoy.
Bruce et al., "Patellar Contact Pressure Changes with Anteromedialization of Tibial Tubercle, Lateral Release, and New Technique for Elevating Quadriceps Tendon: A Biomechanical Study," Journal of Surgical Orthopaedic Advances 22(4), pp. 270-276, 2013.
Office Action dated Jul. 9, 2012, in connection with related European Application No. 10812664, entitled Method and Apparatus for Force Redistributon in Articular Joints, filed Aug. 27, 2010, Cotera, Inc.
Maquet, P., Biomechanical Treatment of Patellofemoral Osteoarthritis. Advancement of the Patellar Tendon; Review of Rheumatism and Osteoarticular Diseases, National Library of Medicine, Dec. 1963, vol. 30, Issue 12, pp. 780-785.
Maquet, Paul G.J., Biomechanics of the Knee With Application to the Pathogenesis and the Surgical Treatment of Osteoarthritis; Springer-Verlag Berlin Heidelberg New York, 1976, pp. 134-204.
Sridhar et al., Obesity and symptomatic osteoarthritis of the knee, The Journal of Bone & Joint Surgery, Instructional Review, vol. 94-B, No. 4, Apr. 2012, pp. 433-441.
Lasmar, et al., Importance of the Different Posterolateral Knee Static Stabilizers: Biomechanical Study; Clinics 2010; 65(4) pp. 433-440.
Hunter, David et al., Alignment and Osteoarthritis of the Knee, Journal of Bone and Joint Surgery, 2009: 91 Suppl. 1:85-9, pp. 85-89.
Halbrecht, Jeffrey L., Arthroscopic Patella Realignment: An All-Inside Technique, Arthroscopy: The Journal of Arthroscopic and Related Surgery, vol. 17, No. 9 Nov.-Dec. 2001; pp. 940-945.
Arnold, Allison S., et al., Do the hamstrings operate at increased muscle-tendon lengths and velocities after surgical lengthening? Journal of Biomechanics, Mar. 2005; pp. 1-9.

(56) References Cited

OTHER PUBLICATIONS

Unnanuntana, Aasis et al., Management of chronic lateral instability due to lateral collateral ligament deficiency after total knee arthroplasty: a case report; Journal of Medical Case Reports, 2010, 4:144; pp. 1-5.

Maquet, P., Biomechanical Aspects of the Relationship between Femur and Patella, Z. Orthop. 112 (1974); pp. 620-623.

Kwak, et al., Hamstrings and Iliotibial Band Forces Affect Knee Kinematics and Contact Pattern, Journal of Orthopaedic Research, 18: 101-108; The Journal of Bone and Joint Surgery, Inc. 1999.

Maquet P., Reduction of the articular pressure of the hip by surgical lateralization of the greater trochanter, PMID: 1015273, Clin Orthop Relat Res. Mar.-Apr. 1977; (123): 138 (Abstract only).

Maquet P., Importance of the position of the greater trochanter, PMID: 2382566, Acta Orthop Belg. 1990; 56 (1 Pt. B): 307 (Abstract only).

Maquet, Paul, "Advancement of the Tibial Tubersosity," Clinical Orthopaedics and Related Research, No. 15, 1976, pp. 225-230.

Townsend et al., "The Biomechanics of the Human Patella and its Implications for Chodromalacia," Journal of Biomechanics, 1977, vol. 10, pp. 403-407.

Supplementary European Search Report dated May 23, 2012 for related application EP10812664 filed Aug. 27, 2010, entitled "Method and Apparatus for Force Redistribution in Articular," Cotera, Inc.

PCT International Search Report and Written Opinion dated Oct. 20, 2010, for related application PCT/US2010/046996 filed Aug. 27, 2010 entitled "Method and Apparatus for Force Redistribution in Articular Joints"; Vivek Shenoy, Mark Deem and Hanson Gifford.

Office Action dated May 17, 2012, in connection with related U.S. Appl. No. 13/002,829, filed Jan. 6, 2011, Shenoy.

Office Action dated Jul. 24, 2012, in connection with related U.S. Appl. No. 12/870,462, filed Aug. 27, 2010, Shenoy.

Final (Rejection) Office Action dated Jan. 31, 2013, in connection with related U.S. Appl. No. 13/002,829, filed Jan. 6, 2011.

\* cited by examiner

Anterior view

Anterior view

Coronal Section

Anterior view

Posterior view

Anterior view

Anterior view

METHOD AND APPARATUS FOR ALTERING BIOMECHANICS OF THE SHOULDER

RELATED APPLICATION DATA

This application claims the benefit of priority of U.S. Provisional Patent Application Ser. No. 62/242,099, filed Oct. 15, 2015, and titled Method and Apparatus for Altering Biomechanics of Articular Joints. This application is also a Continuation-in-Part of U.S. Nonprovisional patent application Ser. No. 13/002,829, filed on Jan. 6, 2011, and titled Method and Apparatus for Force Redistribution in Articular Joints, which is a 371 of International Application No. PCT/US10/46996, filed Aug. 27, 2010, and which claims the benefit of priority of U.S. Provisional Application No. 61/237,518, filed Aug. 27, 2009, and of U.S. Provisional Application No. 61/288,692, filed Dec. 21, 2009. This application is also a Continuation-in-Part of U.S. Nonprovisional patent application Ser. No. 15/017,098, filed on Feb. 5, 2016, and titled Method and Apparatus For Altering Biomechanics of Articular Joints, which is a Continuation application of U.S. Nonprovisional patent application Ser. No. 13/843,128, filed on Mar. 15, 2013 (now U.S. Pat. No. 9,278,004); which application was a Nonprovisional of and claims priority to U.S. Provisional Patent Application Ser. No. 61/620,756 filed on Apr. 5, 2012 and U.S. Provisional Patent Application Ser. No. 61/695,406, filed on Aug. 31, 2012; U.S. Nonprovisional patent application Ser. No. 13/843,128 was also a Continuation-in-Part of U.S. Nonprovisional patent application Ser. No. 12/870,462, filed on Aug. 27, 2010 (now U.S. Pat. No. 8,597,362), which claims priority to U.S. Provisional Patent Application Ser. No. 61/237,518, filed Aug. 27, 2009, and U.S. Provisional Patent Application Ser. No. 61/288,692, filed Dec. 21, 2009. Each of these applications is incorporated herein by reference in its entirety.

FIELD OF THE INVENTION

The present invention generally relates to the field of orthopedics. In particular, the present invention is directed to an interventional technique and implants for altering biomechanics of articular joints to provide a therapeutic effect. More particularly, embodiments of the present invention are directed to alleviating joint pain, effects of osteoarthritis ("OA") and increasing stability in the shoulder.

BACKGROUND

The human body contains many joints that permit articulation of varying degrees between bones. Those that permit free articulation are referred to as diarthroses. Examples include the hip, knee, elbow and shoulder. A variety of connective tissues are associated with the diarthroses joints, including intra-articular cartilages that provide cushioning and smooth sliding surfaces, ligaments that provide flexible connections between bones, and tendons that slide over joints and connect the muscles to provide motion. When connective tissues are compromised, joint pain and loss of function can result.

Osteoarthritis, or OA, is one of the most common causes of disability in the United States. OA is sometimes referred to as degenerative, or wear and tear, arthritis. OA is characterized by the breakdown of the articular cartilage within the joint. Over time, the cartilage may wear away entirely, resulting in bone-on-bone contact. Since bones, unlike cartilage, have many nerve cells, direct bone contact can be very painful to the OA sufferer. In addition to the pain and swelling, the OA sufferer can experience a progressive loss of mobility at the joint. This is due to loss of the joint space, where the articular cartilage has completely worn away.

Currently, various medications are often recommended to reduce the swelling and pain of OA. Other treatments such as weight loss, braces, orthotics, steroid injections and physical therapy may also help alleviate pain and restore function by strengthening muscles supporting the joint. However, since articular cartilage is avascular, or lacks a blood supply, repair and growth of adult cartilage is minimal. If the pain or immobility becomes too severe and other therapies do not alleviate the symptoms, surgical interventions become necessary. Surgical treatments include arthroscopy to clean the joint by removing loose fragments, osteotomy, or joint replacement.

Shoulder Anatomy

There are two joints in the shoulder. The gleno-humeral joint (also called the shoulder joint) is a ball-and-socket joint formed by the scapula and the head of the humerus bone (FIGS. 1A-E). This joint allows the shoulder to move forward and backward and the arm to move in a circular motion. The "socket" (the glenoid fossa of the scapula) is shallow, covering only a third of the "ball" (the head of the humerus). The socket is deepened by the glenoid labrum (see, e.g., FIG. 1C). The labrum is a fibro-cartilaginous rubbery structure that encircles the glenoid cavity effectively deepening the socket to increase static stability of the gleno-humeral joint. The acromioclavicular joint is formed by a part of the scapula called the acromion and the clavicle (see, e.g., FIG. 1A).

The acromioclavicular joint capsule is a soft tissue envelope that encircles the gleno-humeral joint and attaches to the scapula, humerus, and head of the biceps. It is lined by a thin, smooth synovial membrane.

The rotator cuff is a group of four tendons that connects muscles from the scapula and allows the shoulder to rotate and elevate. The four rotator cuff muscles—the subscapularis, supraspinatus, infraspinatus and teres minor muscles—provide support for the gleno-humeral joint.

The deltoid muscle (see, e.g., FIGS. 1B-C) is the largest, strongest muscle of the shoulder. It originates in three portions, the anterior, middle and posterior portions. The anterior portion flexes and medially rotates the arm, the middle portion abducts the arm and the posterior portion extends and laterally rotates the arm. The deltoid muscle takes over lifting the arm once the arm is away from the side of the body.

Rotator cuff tears, the most common injury of the shoulder, cause morphologic changes to cuff tendons and muscles, which can alter muscle architecture and moment arm. These alterations can affect shoulder performance in terms of muscle force and joint strength. Rotator cuff tears are often accompanied by tears in the glenoid labrum due to the alterations in the biomechanics of the shoulder joint.

SUMMARY OF THE DISCLOSURE

Selectively-placed implants are used to address pathologies of joints arising from improper force distribution. By using appropriately sized and positioned implants as described herein, displacement of targeted connective and muscle tissues surrounding the joint is accomplished in order to realign force vectors and/or alter moment arms loading the joint to achieve therapeutic effects without cutting bone and with minimal cutting of the connective tissues.

Exemplary methods disclosed herein comprise selecting at least one of the muscles and connective tissues associated with the shoulder joint as target tissue for treatment, and displacing the target tissue without severing the bones or target tissue, thereby redistributing loading in the joint to achieve a therapeutic effect.

In some embodiments of the invention, increased forces can be selectively applied to one side of a joint by forcing select muscle and/or connective tissues (target tissues) around a longer or more angled path, thus increasing the magnitude, altering the effective direction, and/or changing the moment arm of forces exerted by such muscles or tissues on the joint. This may be accomplished, for example, by appropriately-shaped implants that may be placed under selected target tissues relatively non-invasively compared to current surgical techniques for addressing such conditions. For example, in one embodiment, the implant may be secured to the humerus to increase stability in the shoulder.

In exemplary embodiments, the target tissue is displaced by placing an implant in contact with the target tissue. The implant may be secured to a bone and/or to soft tissues, which may include the target tissue. In a preferred embodiment, the implant reduces a load in a joint that includes the same bone to which the implant is secured. For example, the implant may be secured to the humerus in order to reduce or redistribute a load on an articular surface of the shoulder.

In another embodiment, the load is reduced on a region of the labrum on the glenoid. In one exemplary embodiment, the implant is completely outside the capsule surrounding the joint.

In some embodiments, the implant is secured on a first side of a joint to displace tissue on the first side of the joint in order to reduce a load on an opposing side of the joint. For example, the implant may be secured on a lateral side of the shoulder in order to beneficially alter loads or increase stability in the shoulder on the medial side.

In still further embodiments, connective tissue near a joint is displaced such that a moment arm through which the connective tissue acts upon the joint is increased. An implant may be secured to a bone near the joint such that the implant displaces the connective tissue sufficiently to increase the moment arm.

In preferred embodiments, connective tissue near a joint is displaced sufficiently to achieve a therapeutically effective reduction in a load in the joint. Usually loads will be reduced at least about 5%, preferably at least about 10%, more preferably at least about 15%. The magnitude of displacement required to achieve these load reductions will vary depending upon the joint, size and condition of the patient, and other factors.

In one embodiment for treatment of the shoulder joint, the target tissue may comprise the deltoid muscle. Such an embodiment of an implant is anchored onto the proximal shaft of the lateral humerus, and the deltoid muscle around the humeral head is displaced laterally, antero-laterally, or posterolaterally. The implant may include a fixation portion that is anchored by means of screws or other fixation devices to the humerus. A displacement portion coupled to the fixation portion may be positioned between the bone and the deltoid muscle so as to atraumatically engage and displace the deltoid muscle from its natural path to a therapeutic path, whereby loads in the shoulder joint are redistributed. The deltoid muscle may be displaced laterally, antero-laterally or in other suitable directions relative to the humerus to achieve a therapeutic effect. In another shoulder treatment embodiment, the target tissue may comprise the biceps brachii tendon, in which case a fixation portion of an implant is anchored onto the proximal shaft of the humerus, and a displacement portion of the implant positioned to displace the biceps brachii tendon in a therapeutic direction, e.g. anteriorly.

In some embodiments the displacement portion is configured to avoid interference with the acromion during arm abduction. The displacement portion may have a cranial end shaped and dimensioned such that the displacement portion is spaced caudally and/or laterally from the acromion when the arm is abducted. For example, cranial end of displacement portion may be concave or flattened. Alternatively or additionally, the cranial end of the displacement portion may be configured to slip under the acromion during arm abduction. In addition, the displacement portion may be curved downward toward the humeral bone to avoid interference with the acromion during abduction of the arm. In such embodiments, the bearing surface may have a curvature about a first axis transverse to the humeral shaft with a first radius, and the cranial end may curve toward the humerus about a second axis parallel to the first axis with a second radius, the second radius being less than the first radius. In other embodiments, the cranial end of the displacement portion may have a tapered thickness so as to pass under the acromion during arm abduction.

By using the implants of the invention, appropriately-sized and positioned as described herein, displacement of targeted connective and muscle tissues surrounding the joint is accomplished in order to realign force vectors and/or alter moment arms loading the joint to achieve therapeutic effects without cutting bone and with minimal cutting of the connective tissues. Alternative and more specific devices and methodologies are described in more detail hereinbelow.

BRIEF DESCRIPTION OF DRAWINGS

For the purpose of illustrating the invention, the drawings show aspects of one or more exemplary embodiments of the invention. However, it should be understood that the present invention is not limited to the precise arrangements and instrumentalities shown in the drawings, wherein:

FIGS. 3A-H are views of an exemplary prosthesis for anterior displacement of the biceps brachii tendon in the shoulder, wherein FIG. 3A is a perspective view, FIG. 3B is an anterior (front) view, FIG. 3C is a lateral (side) view, FIG. 3D is a posterior (back) view, FIG. 3E is a caudal (top) view, and FIGS. 3F-H are further anterior views with the prosthesis implanted on the humerus;

FIGS. 7A-I are views of an exemplary prosthesis for lateral displacement of the deltoid muscle in the shoulder in accordance with embodiments of the present invention, wherein FIG. 7A is a perspective view, FIG. 7B is a top view, FIG. 7C is a side view as seen from the anterior side of the implant, FIG. 7D is a side view as seen from the posterior side of the implant, FIG. 7E is a cross-sectional view of the implant sectioned through line A-A of FIG. 7B, FIG. 7F is a cross-sectional view of an alternative embodiment with two portions having different thicknesses, FIG. 7G is a lateral view implanted on the humerus, FIG. 7H is an anterior view implanted on the humerus, and FIG. 7I is a coronal section through the humerus;

DETAILED DESCRIPTION

Figure 1A:
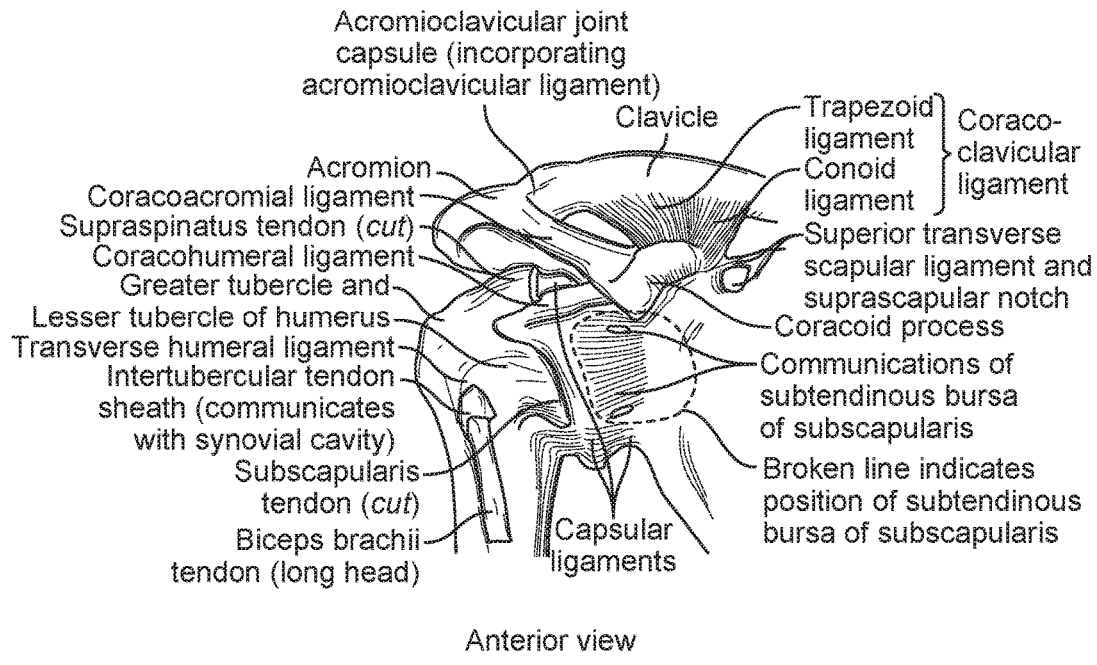
FIG. 1A is a front or anterior view of the shoulder joint with many muscles removed in order to reveal underlying bone, connective tissue and muscle structures.
Figure 1B:
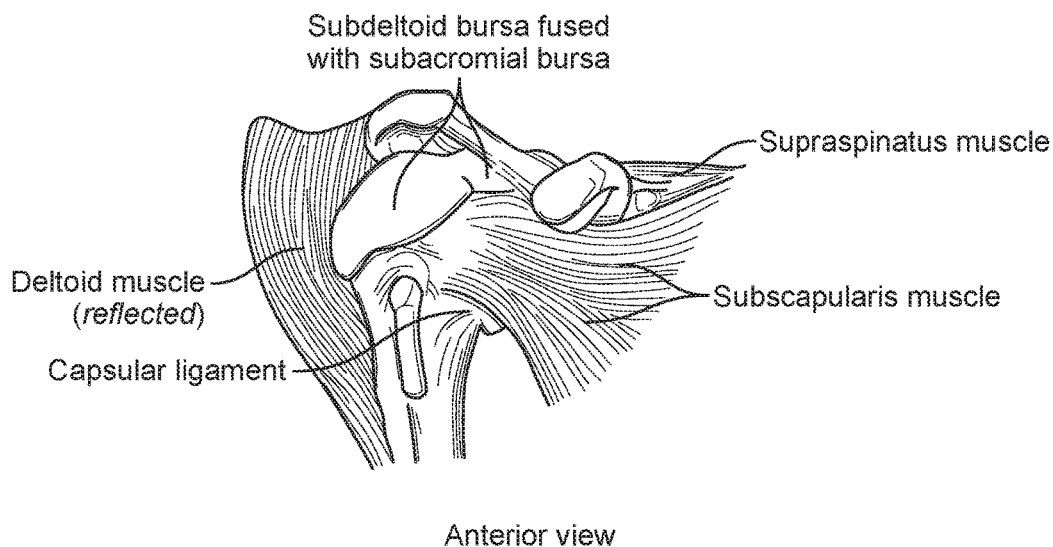
FIG. 1B is a front or anterior view of the shoulder joint.
Figure 1C:
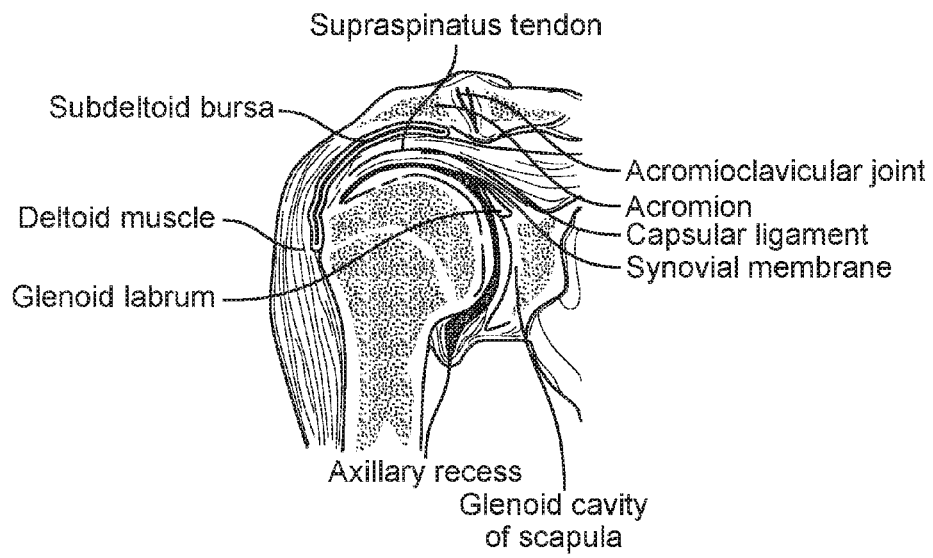
FIG. 1C is a coronal section view of the shoulder joint.
Figure 1D:
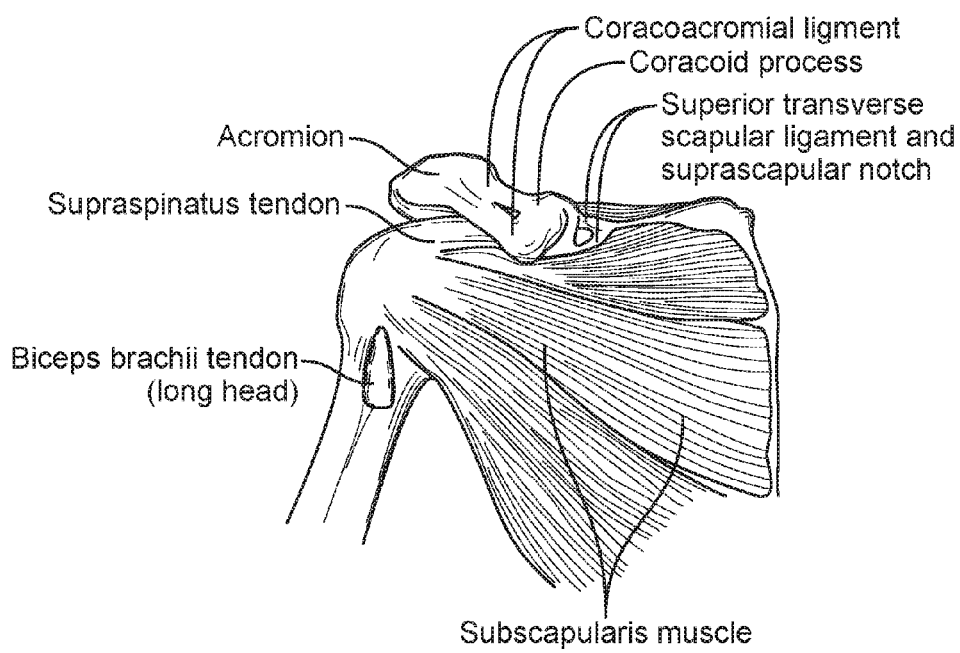
FIG. 1D is an anterior view of the shoulder joint.
Figure 1E:
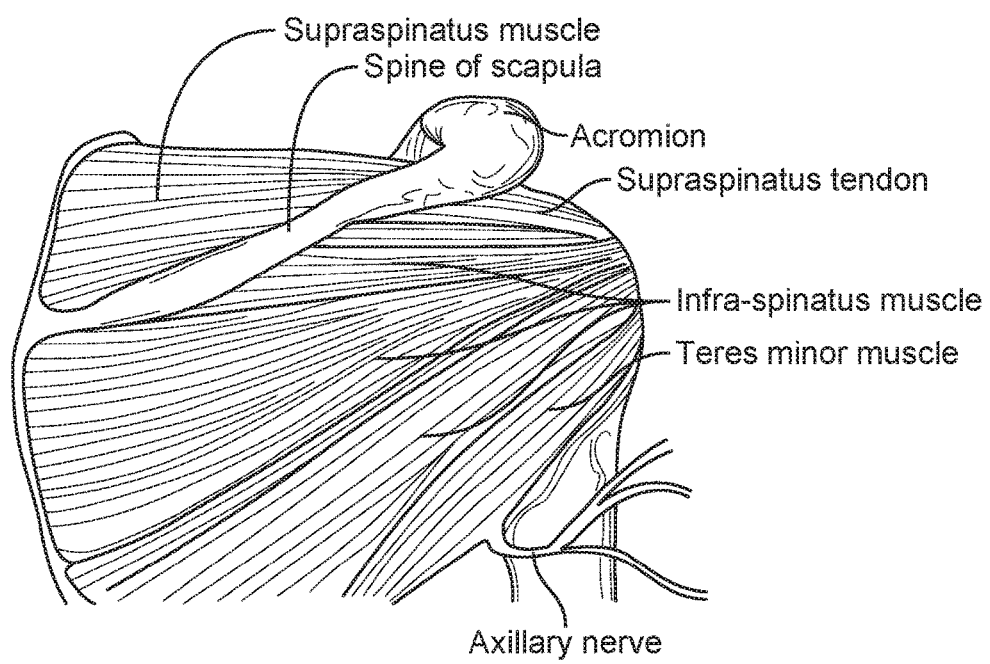
FIG. 1E is a posterior view of the shoulder joint.
Figure 2A:
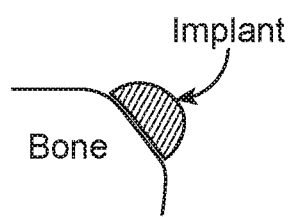
FIGS. 2A, 2B, 2C and 2D are schematic cross-sectional views of a displacement portion of a prostheses according to one embodiment of the present invention.
Figure 2B:
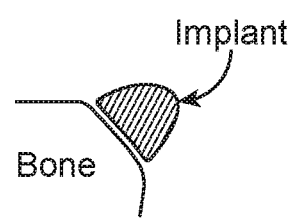
Figure 2C:
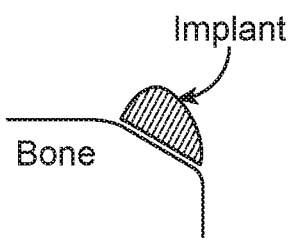
Figure 2D:
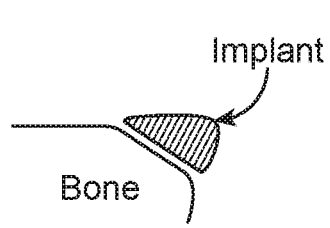

Joint conditions that result from or exacerbate unbalanced force distribution through the joint may be addressed in embodiments of the present invention by interventional techniques involving a redistribution of forces exerted on the joint without the need for highly invasive surgeries requiring significant trauma to the joint and associated muscle and connective tissues. In some embodiments of the invention, increased forces can be selectively applied to one side of a joint by forcing select muscle and/or connective tissues (target tissues) around a longer, more angled or curved path, or other path different from their pre-treatment, natural path, thus increasing the magnitude, altering the effective direction, and/or changing the moment arm of forces exerted by such muscles or tissues on the joint. This may be accomplished, for example, through the use of appropriately-shaped implants that may be placed under or adjacent selected target tissues relatively non-invasively compared to current surgical techniques for addressing such conditions.

Utilizing embodiments of the present invention, joint conditions that result from or exacerbate unbalanced force distribution through the joint may be addressed by interventional techniques involving a redistribution of forces exerted on the joint without the need for highly invasive surgeries requiring significant trauma to the joint and associated muscle and connective tissues. Redistribution of forces within the target joint in accordance with embodiments described herein may thus provide pain relief, slow down articular cartilage degeneration, and/or enhance cartilage regeneration.

The amount of displacement of the target tissue may not need to be large in order to provide a substantial therapeutic effect on the target joint. For example, in the knee, depending upon the nature of the disease and the size and geometry of a particular patient's joint, displacements of greater than about 5 mm up to about 30 mm may be sufficient, with displacements in the range of about 10 mm to about 30 mm also suitable, or more specifically about 10-20 mm. Of course, the specific magnitude and direction of displacement will depend upon the location and type of disease, the target tissue to be displaced, and other factors.

Exemplary embodiments of the invention described herein are particularly directed to treatment of the shoulder, although the principles of the invention may be applied to other joints as described in related co-pending applications and issued patents filed by and/or assigned to the present Applicant. In general, it will be appreciated by persons of ordinary skill in the art that specific features described in connection with one exemplary embodiment may be incorporated in other exemplary embodiments unless otherwise noted. The exemplary embodiments described are thus included to illustrate features of the invention, not limit it. It will be noted by persons of ordinary skill in the art that in some aspects general geometries and methodologies described herein are similar in certain respects to Applicant's prior disclosures with respect to treatment of other joints. However, persons of ordinary skill will also appreciate based on the teachings provided herein and in prior related disclosures that specific differences in configuration, dimension and technique as described herein are necessary for treatment of the shoulder, which is a primary focus of the present disclosure. For example, unlike the knee, the shoulder is a three-dimensional joint so the arm rotates anterior/posterior as well as up/down. To accommodate this greater and more complex range of motion, the area of the bearing surface configured to engage target tissue in the shoulder will typically be larger than in an embodiment configured to treat the knee as described in prior disclosures so target tissue does not slip off the bearing surface when the arm has anterior or posterior orientation. Also, in many shoulder embodiments, advantages may be realized by providing a relatively larger bearing surface area to help reduce tissue irritation and/or more broadly distribute load due to the absence of other interfering structures, such as the patella, which may limit implant size and shape. As another example, the displacement portion and bearing surface in embodiments described herein for treatment of the shoulder will typically be more symmetrical, particularly in the anterior-posterior direction, as compared to embodiments described in prior disclosures related to treatment of the knee.

As used herein, "therapeutic effect" means an effect on a treated joint that reduces forces acting on the articular surfaces, reduces wear, lessens pain, improves stability or provides another positive outcome for the patient whether across the joint as a whole or in particular compartments of the shoulder, knee, or other joint. "Therapeutic effect," however, does not imply, and should not be understood as requiring, any specific, quantified outcome other than as stated above.

As used herein, in humans, dorsal refers to the back of an organism and ventral to the belly. Cranial refers to the head end and caudal to the feet. In humans, anterior is used to indicate the ventral surface and posterior to indicate the dorsal surface. Superior means toward the head and inferior toward the feet. Proximal refers to the end of a structure nearest a major point of reference and distal to the end furthest from a point of reference. The point of reference is usually the origin of a structure (such as a limb). Proximal and distal are relative terms. Medial means nearer the midline of the body and lateral means further from the midline. Superficial refers to structures nearer the skin, and deep to structures further away from the skin. A sagittal plane divides the body into right and left (or medial and lateral) parts. A frontal (or coronal) plane passes from right to left and divides the body into dorsal and ventral (or posterior and anterior) parts. A transverse plane (or cross section) passes perpendicular to the long axis of the body and divides the body into cranial and caudal (head and tail) portions.

Figure 7A:
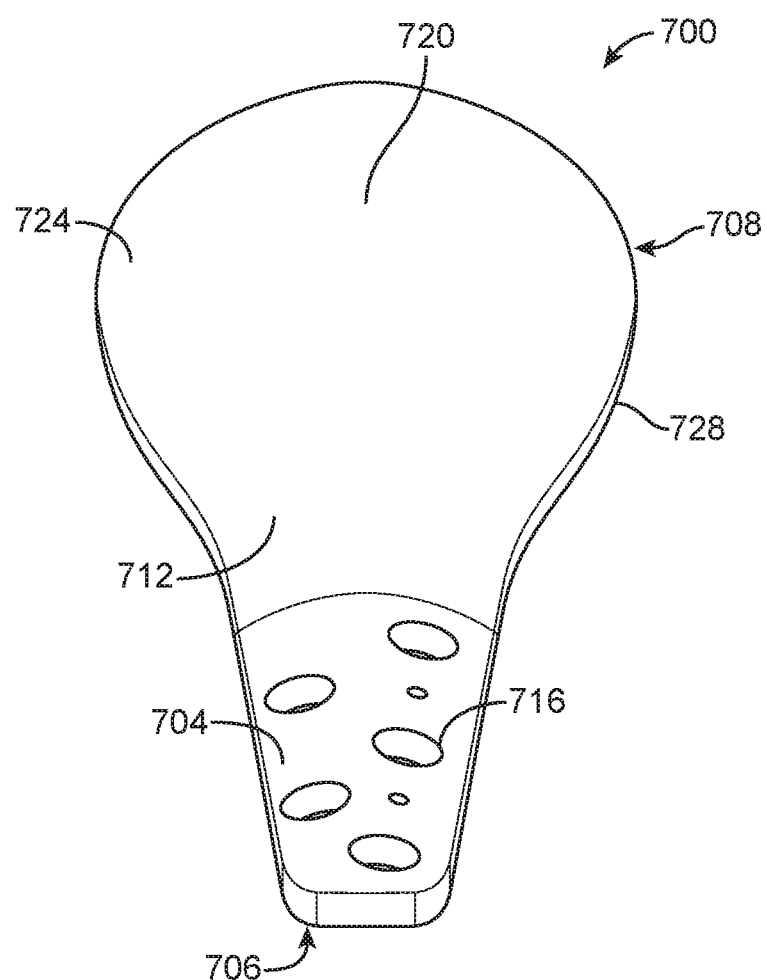
Figure 7B:
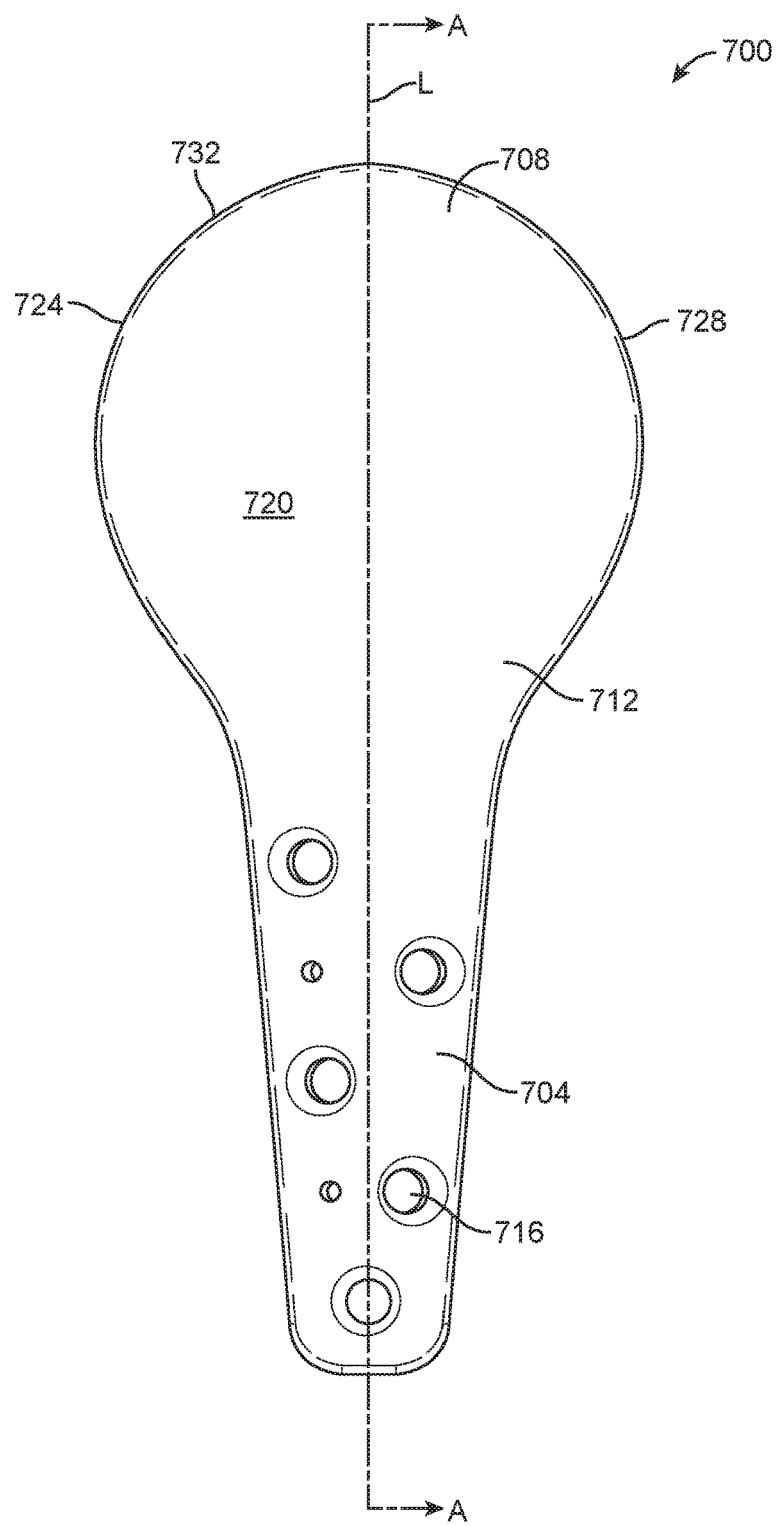
Figure 7C:
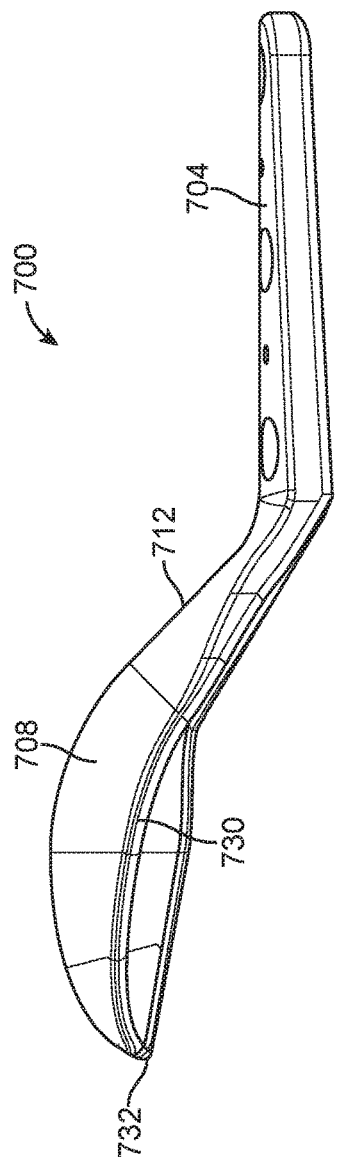
Figure 7D:
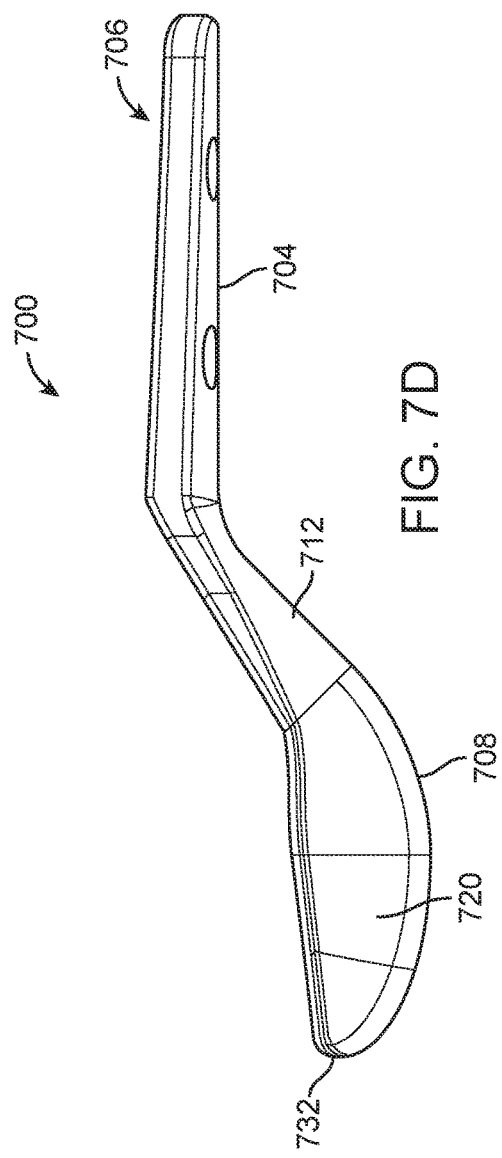
Figure 7E:
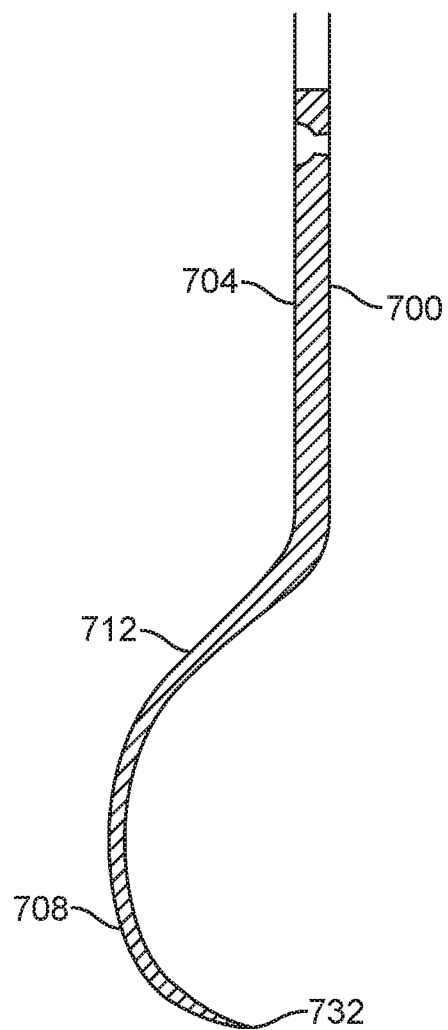

Implants according to embodiments of the present invention may be configured and secured in a variety of ways as described below in more detail with respect to exemplary embodiments. However, in general, and with reference to FIG. 7A, prostheses or implants according to embodiments of the invention will, in preferred embodiments, comprise a fixation portion 704 that provides means for securing or anchoring the prosthesis relative to the joint or tissue, such as holes 716 for bone screws, and a displacement portion 708 configured and dimensioned to displace the target tissue(s) from a pretreatment path as described herein. Other means for securing the fixation portion may include bone ingrowth surfaces, barbs, K-wires, bone cement and other devices known in the art for securing implants to bone. The fixation and displacement portions may be separated by a spanning section 712 that permits those portions to be separated from each other as appropriate to accommodate the anatomical structures between or near the locations of treatment and fixation. The displacement portion 708 may be provided with a bearing member of the same or a different material than the underlying substrate. In some embodiments, again depending on anatomical structures and treatment requirements, two or more of the displacement and fixation portions and spanning section may be merged in whole or in part or may overlay one another.

Depending on the mechanical load on the implant, and the choice of material or materials used to fabricate the implant, thickness of the fixation of the implant typically ranges from about 2.0 mm to 8.0 mm, more typically from about 2.5 mm to 6.0 mm, and may be from about 3.0 mm to 4.5 mm. The thickness of the fixation portion of the implant may be uniform throughout the implant or may vary, e.g., across the implant. Regions of the fixation portion under higher mechanical load may be thicker than regions under lower mechanical loads. The thickness of the fixation region may also be selected to ensure that the screw-heads used to fix the implant do not protrude over the surface of the implant.

The spanning section may have thickness similar to that of the fixation portion. Persons of ordinary skill in the art will appreciate that a principal consideration for spanning section is sufficient structural integrity to maintain the displacement portion at the desired treatment position. Spanning section will usually be rigid, but in some embodiments it may be desirable for the spanning section to have some flexibility and resilience so that it can deflect under sufficient loads. In some cases the spanning section may be adjustable in length or angle relative to the fixation portion and/or displacement portion to allow the operator to configure the device optimally for the particular anatomy and condition being treated. In the displacement portion, displacement distance and thickness may be considered separately. Displacement distance is the distance by which the bearing surface of the displacement portion displaces the target tissue beyond the natural anatomical track of the target tissue, in other words, the displacement of tissue created by the implant. Depending on the particular geometry of the implant, the thickness of the displacement portion may or may not be related to the displacement distance. For example, in an implant with a convex or spoon shaped displacement portion (see, e.g., FIG. 7A-I), or one with a displacement portion that is cantilevered at an angle or stepped into a different plane from the fixation portion or spanning section, the thickness of the material may be substantially less than the overall displacement distance. For example, a material thickness of 4 or 5 mm in the displacement portion may provide sufficient structural integrity for a displacement distance of 25 to 30 mm depending on the material selected. In one embodiment, displacement of the target tissue results in the decrease in the mechanical load on the articular cartilage in the target joint by at least 5%, more preferably by at least 8%, most preferably by at least 10%. Unloading as defined here refers to a decrease in contact forces, either peak forces or average forces, either measured or calculated, during physical activity that results in mechanical loading of articular cartilage in a joint.

The displacement distance provided by the displacement portion of the implant may typically range from greater than about 5 mm to about 30 mm. Of course, the actual displacement distance will depend upon the joint being treated, the location and physical characteristics of the target tissue, the severity and location of disease, and other factors. In some embodiments, displacement distance across the displacement portion may vary. As further examples of how displacement distance and thickness may relate, the displacement portion may be in contact with the underlying tissue and the target soft tissue is displaced by a distance equivalent to the thickness of the displacement portion; thus displacement distance would equal thickness in such an embodiment. In other embodiments, the displacement portion may be elevated above the underlying tissue and the target soft tissue is displaced by a distance greater than the thickness of the displacement region; thus displacement distance is greater than thickness. The surface of the displacement portion also may be contoured to have a curved convex surface in contact with the target soft tissue. For example, the cross-sectional view of the displacement portion may look like a semi-circle or a semi ellipse (see, e.g., FIGS. 2A-D).

Persons of ordinary skill in the art will thus appreciate that a further dimension to be considered is the depth (D) of the implant that governs the magnitude of tissue displacement, e.g., the perpendicular distance from an outermost point on the bearing surface to a point on the fixation surface, that is, the surface of the fixation portion, or the plane in which that surface substantially lies, configured to face the fixation site. Typically, depth (D) will be measured as perpendicular to a plane tangent to an outer most point on the bearing surface, between that plane and a point on the fixation surface that defines the location of fixation to the bone, for example a centerline of the fixation element(s) such as screw holes, provided in the fixation portion.

In alternative embodiments, components of the prosthesis may be a compliant material such as an elastomer, capsules filled with water, saline, silicone, hydrogels, etc. Embodiments with compliant portions could be placed in a deflated state and then inflated to the appropriate thickness. Alternatively, bearing members may be filled with other flowable materials including beads, granules, or other particles made of metal, polymer, or foam material, optionally in a liquid medium, which conform to adjacent bone or tissue surfaces. Thixotropic materials, such as hydrogels derived from hyaluronic acid, change their mechanical properties as shear stress is applied to them. An implant filled with such materials could be made to change the amount of displacement that it provides based on the shear stress that it sees from overlying target tissues at various points across the range of motion of the shoulder. Implants may be coated with materials to reduce friction such as hydrophilic coatings or polytetrafluoroethylene (PTFE) coatings. Additionally or alternatively, the prosthesis may be adjustable to allow the dimensions such as thickness of the prosthesis to be adjusted during surgery or any time after surgery.

Rigid or substantially rigid prostheses according to embodiments of the invention described herein could be made of known bone-compatible implant materials such as titanium or stainless steel. Biocompatible polymers, ceramics, and other materials may also be used. The bearing surface of the prostheses should be designed to minimize negative effects of movement of the connective tissues across the implant surface, e.g., comprising a smooth, atraumatic, low-friction material, coating or surface treatment. Such prostheses could be implanted arthroscopically or using a mini-open or open surgical approach.

In various alternative embodiments, the displacement portion and the fixation portion of prostheses according to the invention may be of unibody construction, or may be formed of two or more distinct parts depending on desired function. For example, the fixation portion may be stainless steel or titanium textured to enhance bony ingrowth and solid screw fixation, while the displacement portion could be made of a different material, for example, pyrolytic carbon to enhance the ability of overlying tissues to slide across the implant, or PTFE, silicone or other low-friction polymer with suitable wear characteristics to provide a softer bearing surface. In this regard, the displacement portion may comprise a separate bearing member with a bearing surface on which the target tissue bears. Alternatively the bearing surface may be formed as an integral part of the displacement portion. In further alternatives, the displacement portion could be comprised of a substrate of one material with an overlying layer forming the bearing member. The substrate could be either attached to or contiguous with the fixation portion. In other embodiments, the fixation portion of the implant may have a relief feature to minimize contact with the underlying bone, thereby minimizing disruption of the periosteal layer.

Generally, the bearing member and/or bearing surface in embodiments of the invention will be hard and smooth, made from materials such as polished pyrolytic carbon, steel, or titanium, or coated or covered with a lubricious material such as PTFE. In such embodiments it is preferable that the bearing surface, which in some cases will comprise the entire displacement portion, be free of screw holes, other hole or gaps, or fixation means generally. However, in embodiments where relative motion is provided for within the prosthesis itself, such as in exemplary embodiments described hereinbelow, the bearing surface may be designed to encourage adhesion and ingrowth of the connective tissue onto this surface. For example, such a surface may be porous, roughened, or configured with openings into which bone or scar tissue may grow to enhance adhesion.

In some embodiments, the implant could be anchored to the underlying bone with suitable fasteners such as screws. Depending on the location and surgical need, unicortical screws, bicortical screws, cancellous screws, cannulated screws, polyaxial screws, screws that lock into the implant, etc., may be used. In some embodiments, the screw holes may be locking threads or other locking features. In other embodiments, the screw holes may be oriented in different directions to improve the stability of the anchored implant. In alternative embodiments, different types of screws may be used in different regions of the implant. For example, cortical screws may be used in the region of an implant in contact with the humeral shaft while cancellous screws may be used in another part of the implant in contact with areas around the humeral tubercles or head. Depending on patient anatomy and geometry of a specific implant, it may be desirable to provide supplemental fixation (such as cancellous bone screws) in the spanning section. As will be understood by persons skilled in the art based on the teachings and descriptions provided herein, fixation by means of bone screws or similar bone-penetrating devices is not a "cutting" of the bone, the avoidance of which is one advantage of the present invention as elsewhere described.

In the present invention, implants may be configured such that the displacement portion of the implant is separated or spaced apart from the fixation portion of the implant. With the displacement portion positioned under the target tissue (e.g., biceps brachii tendon), the fixation portion of the implant may be configured to be affixed to the bone at a location that is suitable for securely fixing the implant in place, is accessible to the surgeon, is not covered by the target tissue, and is separated from tendon insertion points and other anatomical features. The implant may have a spanning section shaped and dimensioned to bridge the distance between the fixation portion and the displacement portion. In exemplary embodiments, the implants may be configured to move the tendon anteriorly or medially or anterior-medially or laterally or antero-laterally. This may be accomplished by making one side (lateral or medial) of the displacement surface higher than the other and/or by forming a track with ridges on one or both sides of the bearing surface to urge the tendon in a lateral or medial direction. The optimal direction and magnitude of displacement may vary patient to patient, depending upon the location and nature of the joint pain, injury, or wear, the tendons targeted for displacement, and other factors as may be determined by the physician in pretreatment assessment, and may be customized for each patient by selection of implant geometry, size, and location of implantation. In some embodiments, implants may be configured to be changed in size or shape by the physician in situ to the ideal shape and size for the patient's particular condition.

Figure 3A:
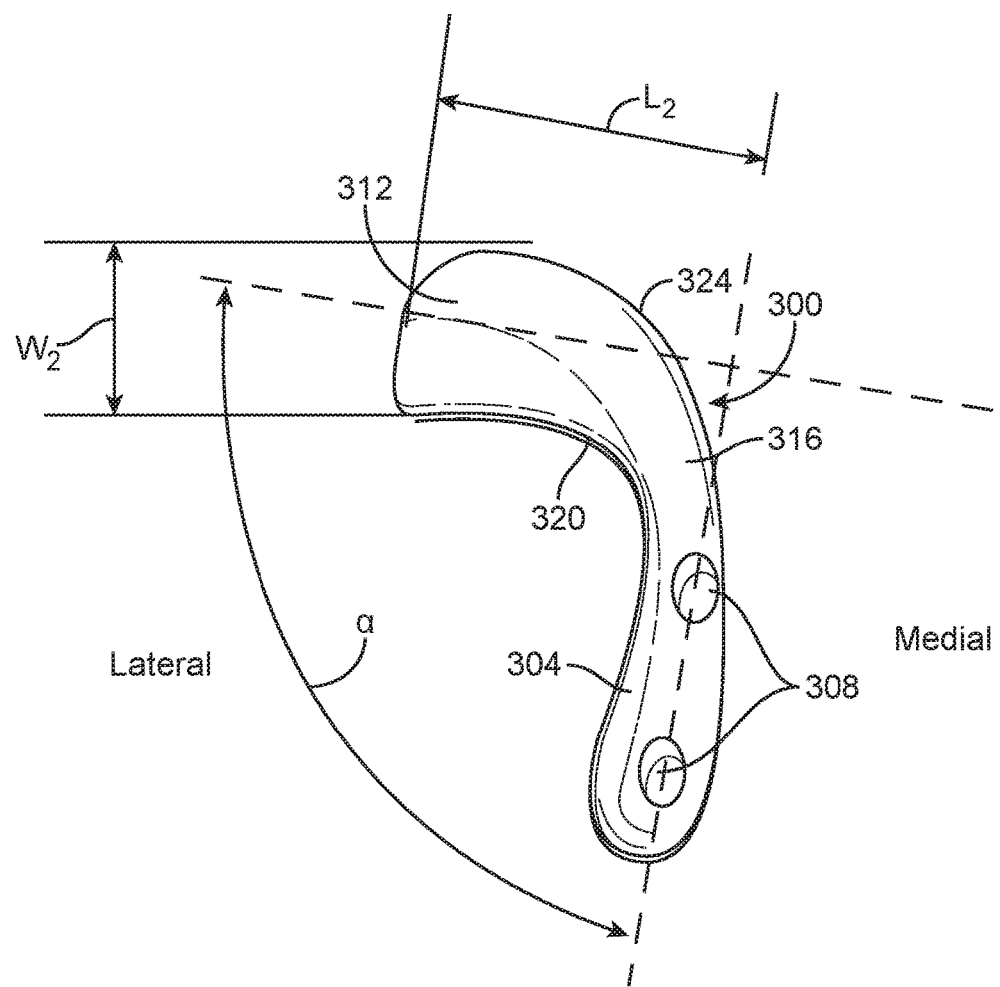

FIGS. 3A-H depict an exemplary prototype of implant 300 for stabilizing or reducing pain in the shoulder. Implant 300 has a fixation portion 304 having one or more holes 308 for receiving screws for anchoring the implant to bone. Fixation portion 304 is generally straight and elongated, being configured for positioning in general alignment with the longitudinal axis of the humeral shaft on the lateral side of the humerus. A plurality of holes 308 are spaced apart longitudinally along fixation portion 304 preferably positioned in approximate alignment with, or on alternating sides of, a longitudinal centerline of fixation portion 304. Displacement portion 312, is configured and dimensioned to be positioned under the target tissue. In the embodiment of FIG. 3A displacement portion 312 extends in a transverse direction relative to fixation portion 304 such that the overall implant has an "L" or "J" shape. The displacement portion 312 is configured to atraumatically engage the target tissue and displace it anteriorly relative to the bone. The displacement portion 312 has a length in the lateral-medial direction selected to accommodate the full width of the target tissue so that the target tissue remains engaged along its entire width as it slides on the displacement portion. Fixation portion 304 will have a length significantly greater than the width W2 of the displacement portion in the cranial-caudal direction (along the axis of the humeral shaft), usually being at least 2-4 times width W2, so as to increase the leverage of the screws used to secure the implant to the bone via holes 308. Displacement portion 312 preferably has a convex curvature on its outer tissue-engaging surface (bearing surface), preferably being curved at least around an axis generally parallel to the bone shaft, usually being curved also around an axis perpendicular to the bone shaft, and more preferably being spherical or partially spherical. Displacement portion 312 has a width, typically less than its length in the caudal-cranial direction, selected so that it does not interfere with other tissues, or engage the insertion/attachment points of surrounding soft tissue structures like the pectoralis major muscle or the latissimus dorsi muscle. A spanning section 316 interconnects fixation portion 304 and displacement portion 312. Spanning section 316, in the embodiment illustrated, extends cranially and laterally from fixation portion 304 to displacement portion 312, forming a curve of about 90° about a dorsal-ventral axis. Where fixation portion 304 is configured for attachment to a more medial aspect of the bone, spanning section 316 will extend ventrally as well as cranially and laterally from fixation portion 304, preferably being curved about an axis generally parallel to the bone shaft. Displacement portion 312 appropriately displaces the target tissue in cooperation with the fixation portion 304 and spanning section 316.

Figure 3B:
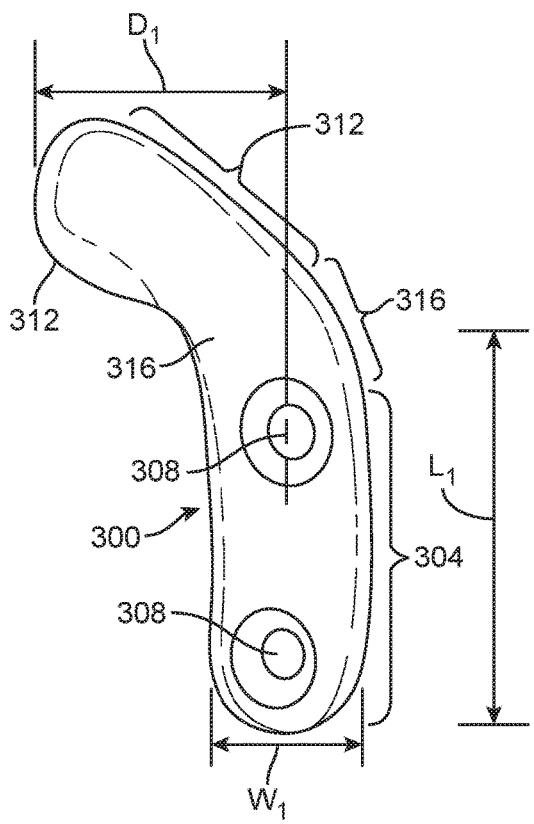
Figure 3C:
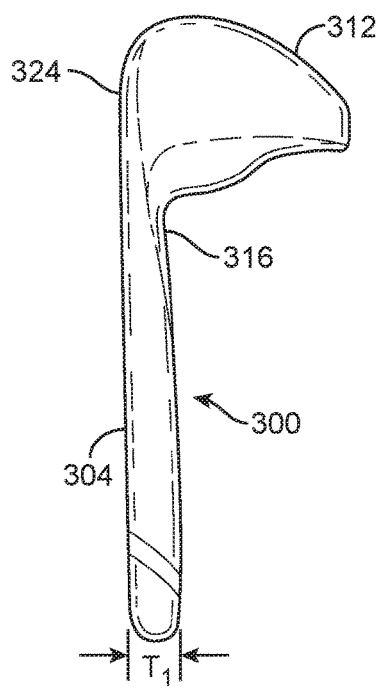
Figure 3D:
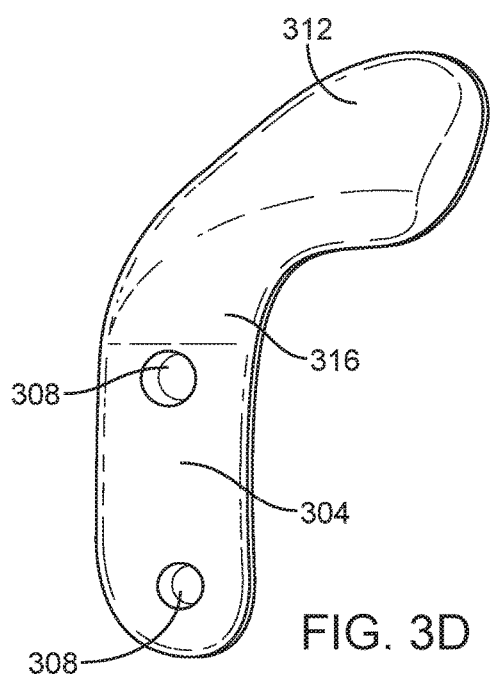
Figure 3E:
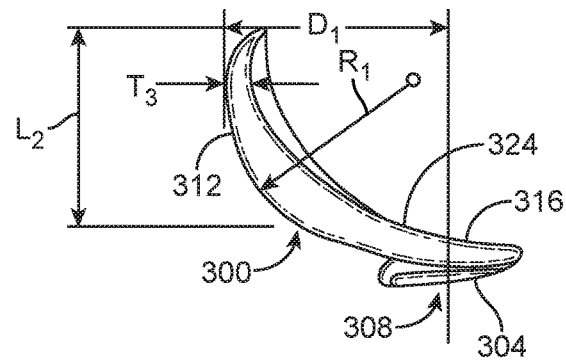

Displacement of the target tissue can be altered by changing the length, curvature and angle of the spanning section among other features. For example, the angle α between the displacement portion 312 and the fixation portion 304 (as measured at the intersection of the center line axes of the two portions in the top view of the implant in FIG. 3A) may range from about 80 degrees to 135 degrees, more specifically from about 85 degrees to 120 degrees, and in some embodiments about 90 degrees to 110 degrees. As shown in FIG. 3B, the width $W_1$ of the fixation portion 304 will be large enough to span a substantial portion of the width of the bone to which implant 300 is affixed and to accommodate one or more screw holes of sufficient size, ranging from about 10 mm to 25 mm, more specifically about 12 mm to 20 mm, and in some embodiments about 14 mm to 18 mm. The length $L_1$ of the fixation portion 304 will be selected to accommodate a sufficient number of screw holes in the cranial-caudal direction along the bone, usually at least two and in some embodiments up to five or more, and may range from about 20 mm to 50 mm, more specifically about 25 mm to 45 mm, and in some embodiments about 30 mm to 40 mm. As shown in FIG. 3A, the width $W_2$ of the displacement portion 312 is selected to provide a broad area of contact with the target tissue to spread the force and reduce wear, while not interfering with joint structures as mentioned above throughout the full range of joint motion. Width $W_2$ may thus range from about 10 mm to 25 mm, more specifically about 12 mm to 20 mm, and in some embodiments about 14 mm to 18 mm. The length $L_2$ of the displacement portion 312 is selected so that the displacement portion extends under the full width of the target tissue so that the entire width of the target tissue remains in engagement and displaced the desired amount throughout the range of joint motion. Length $L_2$ may thus range from about 20 mm to 50 mm, more specifically about 25 mm to 45 mm, and in certain embodiments about 30 mm to 40 mm. Implant depth $D_1$, along with the radius of curvature $R_1$ of the outer surface of displacement portion 312, shown in FIG. 3E, are selected to optimize target tissue displacement throughout the range of joint motion. Radius of curvature $R_1$ is usually 20 mm to 35 mm, more preferably 22 mm to 33 mm, and most preferably 25 mm to 30 mm. For average patient anatomy, an overall implant depth ($D_1$), shown in FIGS. 3B and 3E, as measured from the outermost surface of displacement portion 312 to the centerline of the screw holes in fixation portion 304, would be in the range of 10 mm to 45 mm in order to provide target tissue displacements in the ranges cited hereinabove to achieve a therapeutic effect.

The inferior edge 320 of the spanning section 316 can also be curved to minimize or eliminate any contact with the edge of the biceps brachii tendon when implanted to treat conditions in the shoulder. The superior surface edge 324 of the displacement portion 312 can be curved to allow for easy motion of the tendon during flexion as well as to vary the displacement of the tendon during flexion by varying the region of the implant surface in contact with the tendon at higher flexion angles.

Figure 3F:
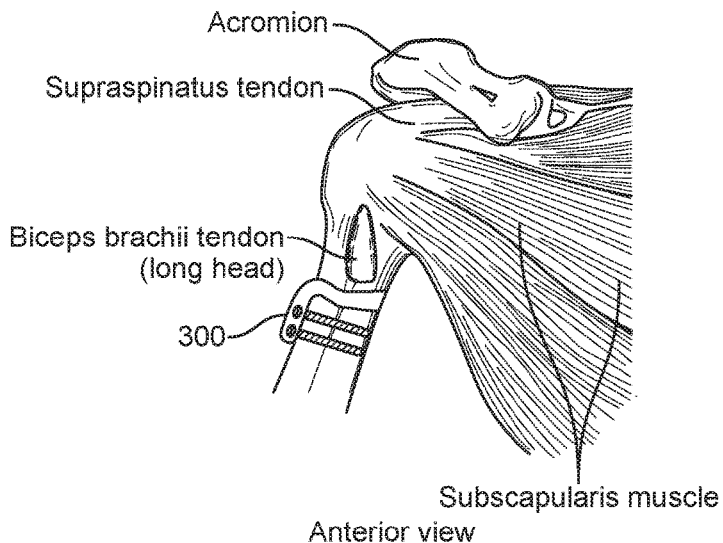
Figure 3G:
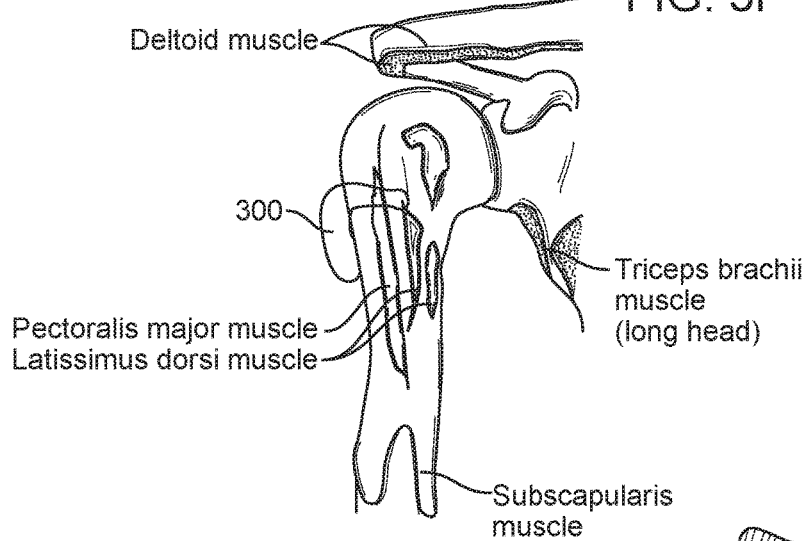
Figure 3H:
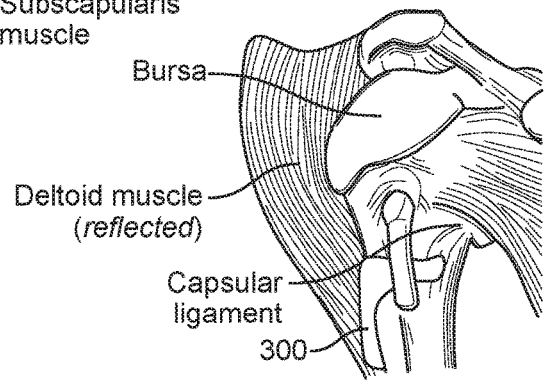

FIG. 3F shows the placement of implant 300 on the lateral side of the proximal humerus to stabilize or treat other conditions in the shoulder by displacing the biceps brachii tendon in an anterior direction. Fixation portion 304 is on the lateral side of the humerus, under the deltoid muscle (see FIG. 3H). Displacement portion 312 goes under the long head of biceps brachii tendon as shown in FIGS. 3F and 3H, and displaces the tendon anteriorly. FIG. 3G shows the attachment points of other muscles in that region. Displacement portion 312 is shaped to avoid the attachment points of the pectoralis major muscle and the latissimus dorsi muscle.

Figure 3I:
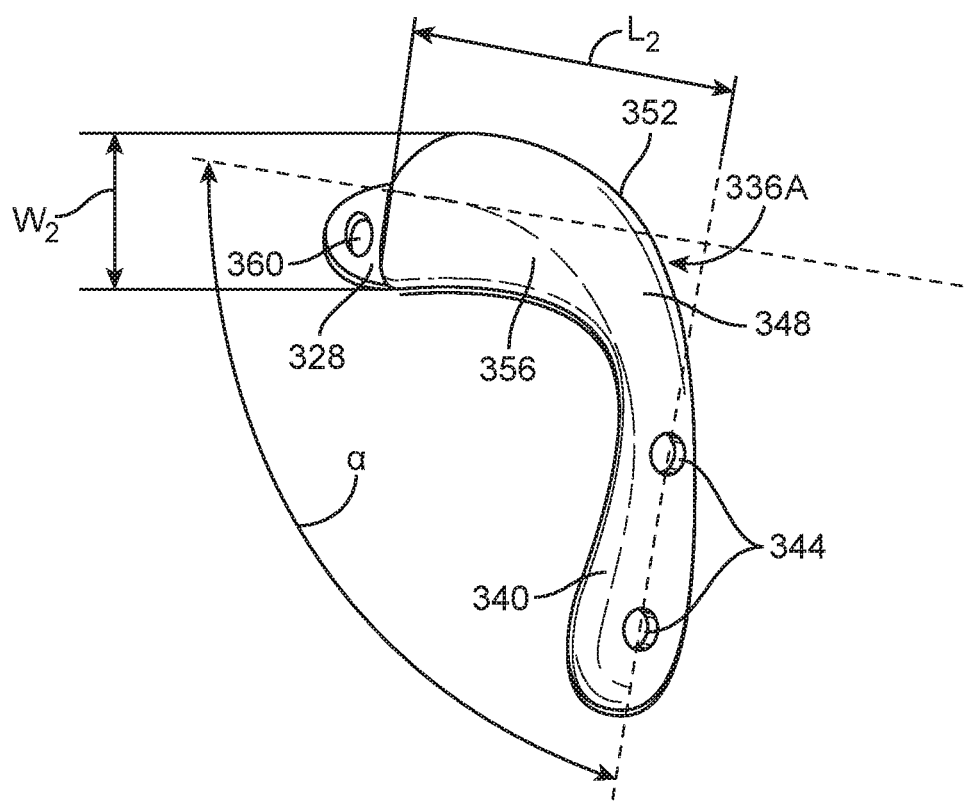
FIGS. 3I and 3J are perspective views of further alternative embodiments employing supplemental fixation/support means.
Figure 3J:
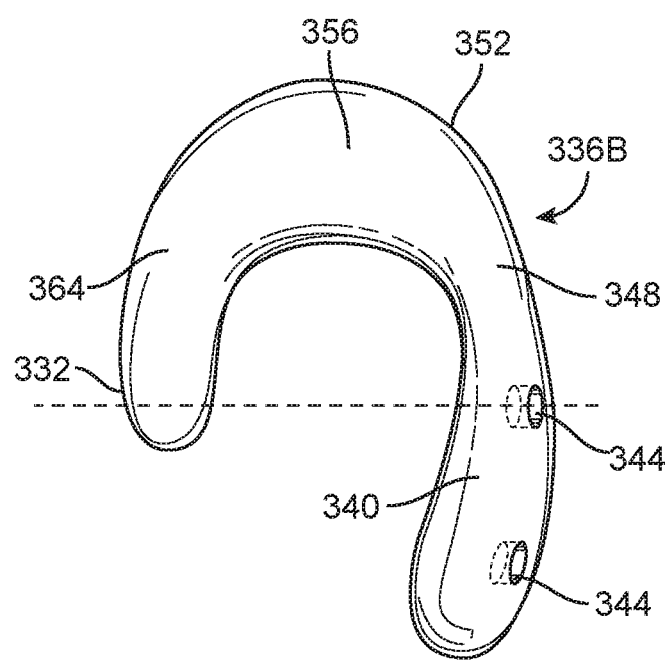

FIGS. 3I and 3J illustrate further alternative embodiments employing supplemental support and fixation elements 328 and 332. Implants 336A and 336B each include fixation portion 340 with fixation means such as bone screw holes 344, spanning section 348 and displacement portion 352 with bearing surface 356. With respect to implant 336A, fixation portion 340 is generally straight and elongated, being configured for positioning in general alignment with the shaft of the humerus. The displacement portion 352 is configured to atraumatically engage the tendon and displace it anteriorly relative to the humerus. The displacement portion 352 has a length in the lateral-medial direction generally selected to accommodate the full width of the tendon so that the tendon remains engaged along its entire width as it slides on the displacement portion. Displacement portion 352 preferably has a convex curvature on its outer tissue-engaging surface (bearing surface 356), preferably being curved at least around an axis generally parallel to the humeral shaft, usually being curved also around an axis perpendicular to the humeral shaft, and more preferably being spherical or partially spherical. Alternatively the bearing surface may have other curvatures such as elliptical, parabolic, logarithmic spiral, or other complex curvature. Positioned at the end of displacement portion 352 on implant 336A is supplemental support and fixation tab member 328 with at least one bone screw hole 360.

In a further embodiment, tab member 328 has no bone screw hole, but simply provides additional surface area resting against the bone surface to stabilize the device and to more widely distribute the pressure of the device due to the force of the tendon against the device.

As illustrated in FIG. 3J, in order to provide supplemental fixation and support means without necessitating a second incision site, an alternative implant such as 336B may be employed. In this embodiment, displacement portion extension 364 extends the displacement portion in a caudal direction around the medial side of the humerus. Supplemental support and fixation tab 332 is disposed at the caudal and/or medial margin of the extended displacement portion. Placement of an embodiment such as implant 336B is achieved by positioning the fixation portion on the lateral side of the humeral shaft with the extended displacement portion 364 extending around the tendon to the humerus and back down caudally on the opposite side of the humeral shaft. A further bone screw fixation hole (not shown) may alternatively be provided on fixation tab 332

Figure 4:
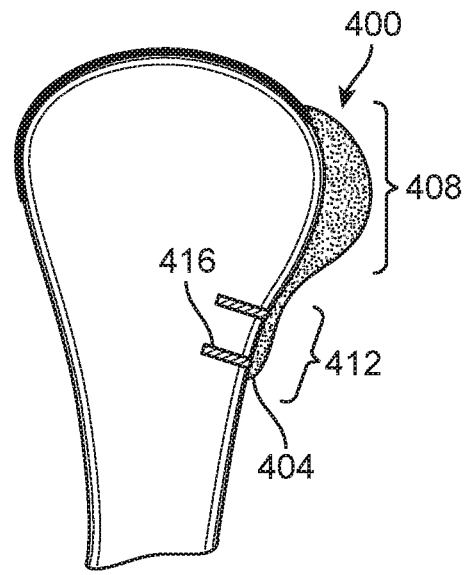
FIG. 4 is a schematic view of the cranial end of the humerus adjacent a shoulder joint with a prosthesis implanted according to an exemplary embodiment of the present invention.

In another exemplary embodiment of the invention, as shown in FIG. 4, prosthesis 400 provides displacement by inserting a passive, space-occupying implant under a target tissue associated with an articular joint. Prosthesis 400 comprises a body member 404 that defines displacement portion 408 and fixation portion 412. Displacement portion 408 is the portion responsible for displacing the target tissues as required to accomplish altering the moment arm of the surrounding target tissue. The bone facing surface of displacement portion 408 is preferably shaped to conform to the external shape of the bone surface on which it is secured and may have a hook- or spoon-like shape on its distal end to wrap partially around the end of a bone such as the end of the humerus at the shoulder. Displacement portion 408 is preferably rounded and smooth on its outer non-bone facing side to provide a smooth surface over which the displaced soft tissues may slide. Fixation portion 412 is shaped so that it lies more flat under the muscles and tendons along the bone spaced from the treated joint, away from the complexity of the areas adjacent to the joint or bone end, where many different tissues crossover and attachments to bone can occur. This more proximal segment of the bone would allow easier access to the underlying bone and potentially better fixation. Fixation could be achieved by any known means for bone-secured implants, such as bone screws 416, tacks, anchors or adhesives, to name a few possibilities. The implant could be made from any suitable material, either hard or soft materials. In this case, silicones of varying grades and durometers, titanium, stainless steel or pyrolytic carbon are examples of materials which would be appropriate choices.

Figure 5:
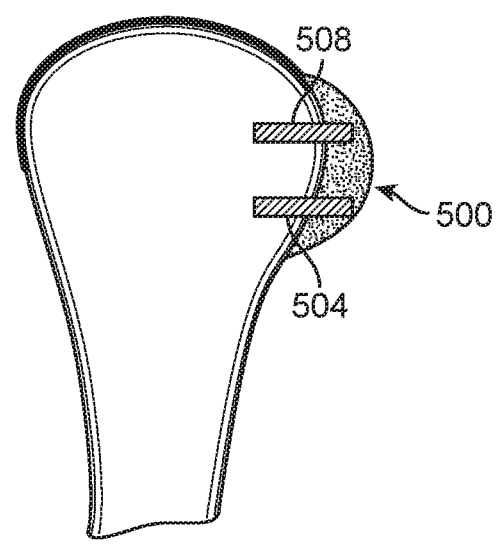
FIG. 5 is a schematic view of the cranial end of the humerus adjacent the shoulder joint with a prosthesis implanted according to an alternative exemplary embodiment of the present invention.

In one alternative embodiment, depending on specific patient conditions, it may be desirable to directly secure the prosthesis to the humerus in the region of the neck, tubercles or head immediately adjacent the articular joint. Prosthesis 500, shown in FIG. 5, illustrates an example of such a prosthesis. In this embodiment, the fixation and displacement portions are collocated within body member 504 closer to the end of the humerus, for example the humeral head. The configuration of the body member with respect to its displacement function would be essentially the same as described above. Fixation would also be substantially as previously described, e.g., using screws 508 or other attachment means, except that it is adapted to allow fixation and displacement functions to be collocated.

Figure 6:
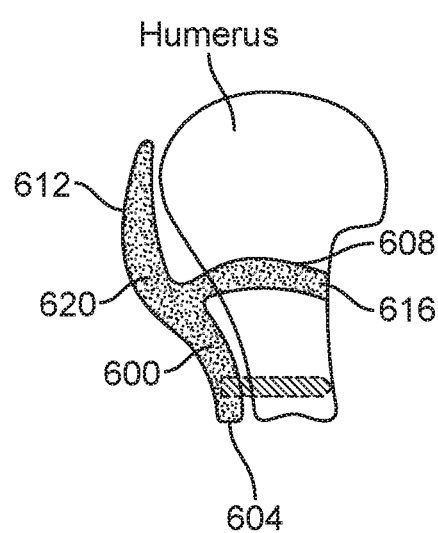
FIG. 6 is an anterior view of a right humerus illustrating positioning of an implant for treatment of shoulder indications requiring lateral and anterior displacements.

In other embodiments of the present invention, apparatus for treating multiple indications with a single implant are disclosed. Examples include treatment of shoulder conditions benefiting from anterior and lateral displacement of target tissues such as the deltoid muscle and biceps brachii tendon. FIG. 6 depicts an exemplary embodiment of a humeral implant to treat the shoulder. These embodiments are alternatives to placing separate implants, also disclosed herein. The dimensions of the implant would preferably be similar to the dimensions of the implants to treat single indications described in connection with exemplary embodiments of the present invention discussed herein. The fixation portion of a multiple indication treatment implant may be subject to higher mechanical forces compared to single compartment treatment implants. To withstand the higher mechanical loads, the fixation portion may preferably be thicker, wider or longer as may be selected by a person skilled in the art based on the teachings contained herein.

In the embodiment of FIG. 6, fixation portion 600 may be used to anchor implant 604 onto the humerus, first displacement portion 608 may displace the biceps brachii tendon and second displacement portion 612 may displace the deltoid muscle. In some embodiments, the implant is anchored only on the lateral side of the humerus, thereby allowing the implantation procedure to be performed by a single incision. In other embodiments, the opposite side may also be anchored with supplemental fixation 616 using a percutaneous technique, for example, by using a percutaneous screw. The displacement of the target tissue can be altered by changing the thickness, length, curvature and angle of the spanning section and/or displacement portion and other aspects of the implant as described herein. First displacement portion 608 may be configured to move the tendon anteriorly or medially or anterior-medially or laterally or antero-laterally. This may be accomplished by making one side (lateral or medial) of the displacement. surface higher than the other, and/or by forming a track with ridges on one or both sides of the bearing surface to urge the tendon in a lateral of medial direction. The inferior region of the displacement sections may be contoured to substantially conform to the curved anterior surface of the humerus. First displacement portion 608 also may be designed to be in contact with the underlying bone or could be elevated so as to avoid contact with the underlying bone, thereby not disrupting the periosteal layer. Spanning section 620 may be configured in a general y-shape such that first displacement portion 608 is generally orthogonal the fixation portion 600. The first arm of spanning section 620 may extend at an angle laterally and anteriorly from fixation portion 600. First arm of spanning section 620 extends first displacement portion 608 out anteriorly to achieve the necessary displacement. The spanning section second arm also may be configured to hold the second displacement portion 612 in a position spaced-apart from the underlying surface of the humerus to avoid any connective tissue underneath the displacement portion. The spanning sections may also comprise adjustable mechanisms (e.g., a pin, slot, or hinge) to movably or pivotably alter the orientation or angle between the two parts to achieve the appropriate level of tissue displacement.

Figure 7F:
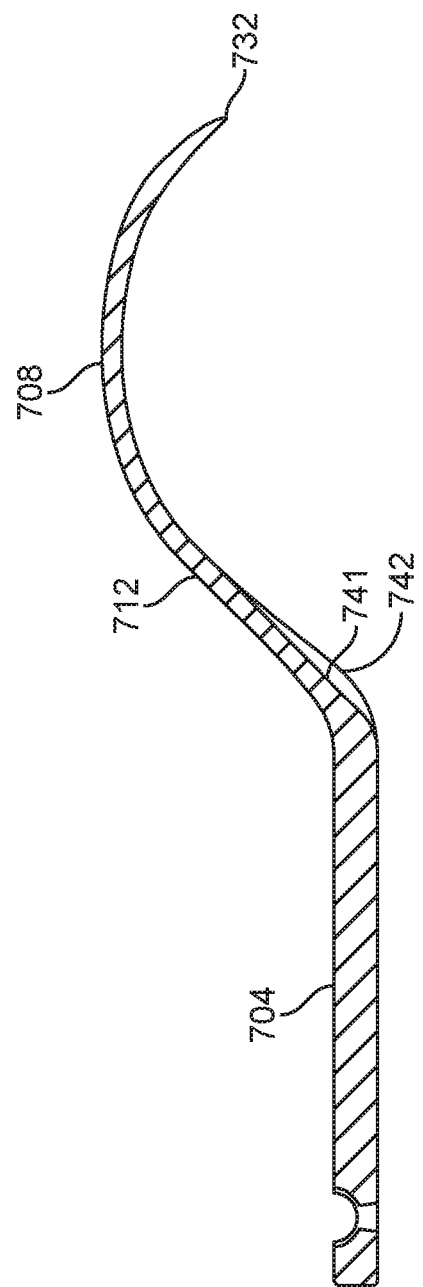
Figure 7G:
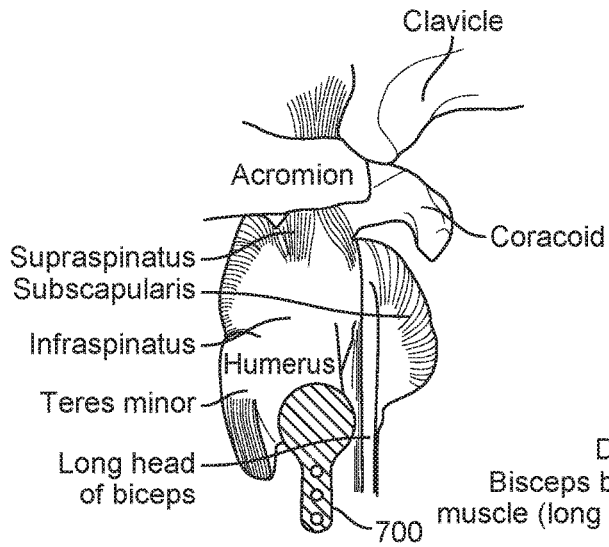
Figure 7H:
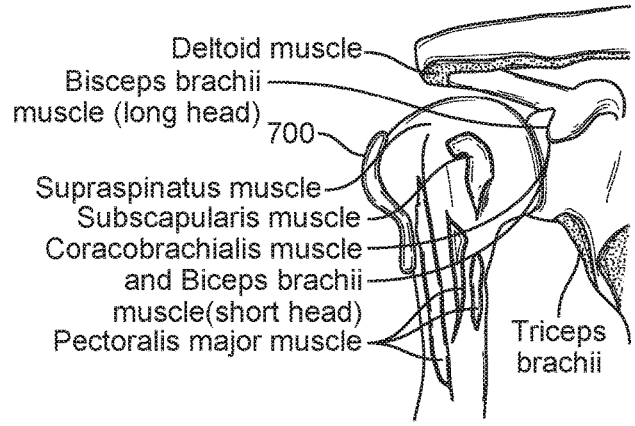
Figure 7I:
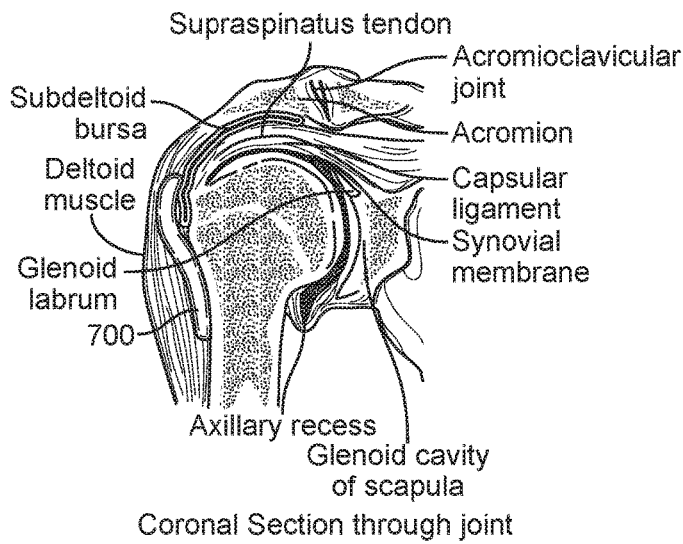

FIGS. 7A-I show exemplary embodiments of the present invention for displacement of the deltoid muscle. FIGS. 7A-E schematically depict implant 700, FIG. 7F depicts an alternative cross-section and FIGS. 7G-I schematically depict implant 700 anchored on the lateral side of the humerus. In general, and consistent with other implants described herein, implant 700 includes fixation portion 704 to anchor the implant and displacement portion 708 to displace the target tissue, e.g., deltoid muscle. The fixation portion and the displacement portion are connected by spanning section 712. Screw or screws in screw holes 716 in fixation portion 704 secure the implant.

As shown in FIGS. 7A-I, fixation portion 704 is configured and dimensioned for attachment of the implant to the humerus, preferably on the lateral side of the proximal humeral shaft just below the humeral head. The implant may be attached with screws positioned in the screw holes 716. Displacement portion 708, the region for displacing the target tissue, typically the deltoid muscle in this embodiment, is connected to fixation portion 704 through spanning section 712. The displacement of the tissue can be altered by changing the length, shape, and angle of the spanning section 712, the shape, thickness and orientation of displacement portion 708, and other aspects of the implant as described herein. In exemplary embodiments, a material thickness of 4 or 5 mm in the displacement portion may provide sufficient structural integrity for a displacement distance of 25 to 30 mm depending on the material selected.

In this exemplary embodiment, fixation portion 704 comprises a generally elongated section of the implant, specifically configured and dimensioned based on patient anatomy to be oriented along the longitudinal axis of the humeral shaft. An inner, bone engaging surface 706 of fixation portion 704 has a concave curvature about its longitudinal axis generally matching that of the outer surface of the humerus to maximize surface contact between fixation portion 704 and the underlying bone. A plurality of screw holes 716 are spaced longitudinally along fixation portion 704 and extend through fixation portion 704 such that screws may be inserted through them in a medial direction into the humerus. Displacement portion 708 is preferably separated or offset from fixation portion 704. In the embodiment illustrated, spanning section 712 extends laterally and cranially from fixation portion 704 to displacement portion 708. Displacement portion 708 is attached along its cranial extent to spanning section 712, with its opposing cauda edge being a free end. In this way implant 700 may be fixed to the bone only at its caudal end, where fixation portion 704 is located, while remaining unattached to the bone at its free end where displacement portion 708 is located. Of course, in some embodiments implant 700 may have one or more additional fixation portions, such that implant 700 may be secured to the bone at both ends or along its edges.

Displacement portion 708 preferably has an enlarged spoon-like rounded shape similar to the lateral profile of the humeral head adjacent the gleno-humeral joint. In some embodiments, fixation portion 704 has a length selected to extend longitudinally along the bone to which it attached sufficiently to stabilize the implant and to accommodate the desired number of hole(s) to receive screws for anchoring to the bone. The length of fixation portion 704 provides space for multiple screw holes and allows the screw holes to be located a significant distance apart from displacement portion 708 so as to maximize the leverage of the fixation screws in counteracting the force of the tissue on the displacement portion. In some embodiments the length of the fixation portion will be substantially greater than the length from the cranial extent of fixation portion 704 to the cranial edge 732 of displacement portion 708, with the fixation portion length being generally in the range of 25 mm to 55 mm in exemplary embodiments.

In preferred embodiments of implant 700, the combined length of the spanning section 712 and displacement portion 708 will be selected to position the displacement portion under the deltoid muscle laterally of the humeral head. Displacement portion 708 preferably has a convex curvature on its outer or lateral side (bearing surface 720), and a concave curvature on its inner side 730. Displacement portion 708 has an outer bearing surface 720, which engages the target tissue (e.g., deltoid muscle). Bearing surface 720 typically will be smooth, rounded and low-friction to minimize wear and trauma to the tissue targeted for treatment. In preferred embodiments, bearing surface 720 is free of significant ridges, bumps, voids, holes or other discontinuities of the kind that would cause abrasion or wear of the target tissue, particularly larger holes or channels for fixation devices such as screws or K-wires. Bearing surface 720 may comprise simply a smoothed and/or polished region of displacement portion 708, or it may comprise a coating or layer of a different material, e.g., a lubricous biocompatible polymer. In other embodiments, bearing surface 720 may have holes, protuberances, a polymeric or drug coating, or other features to promote adhesion with the displaced target tissue such that movement between the target tissue and implant 700 is minimized.

Preferably the inner and outer surfaces of the displacement portion have curvature about multiple axes, and may be generally or partially spherical. The radius of curvature of the outer surface, is selected to provide the optimal displacement of the target tissue throughout the range of motion of the shoulder joint (flexion/extension, abduction/adduction, internal/external rotation). In some embodiments the shape and curvature of the outer surface will be selected such that the target tissue is under a substantially constant magnitude of displacement throughout the range of joint motion, while in other embodiments, the shape and curvature of the outer surface will be selected to displace the tissue more in certain portions of the range of motion, while reducing the displacement in other regions of the range of motion. Curvature of the outer surface of displacement portion 708 is usually at a radius in a range of about 15 mm to 35 mm. The curvature of the surface may also be selected to avoid contact with the acromion during shoulder abduction.

Displacement portion 708 may be cantilevered or suspended by spanning section 712 in a plane laterally displaced from or angled relative to fixation portion 704 such that it is spaced apart from the lateral surface of the bone when the implant is fixed in its implanted position. This provides space between humeral head and the displacement portion through which non-target soft tissues may reside and/or move without interference. In a preferred embodiment, spanning section 712 extends laterally and cranially at an oblique angle relative to fixation portion 704 such that a plane tangent to the surface of the spanning section 712 is disposed at an angle in the range of about 30° to 60° relative to a centerline through fixation portion 704.

Spanning section 712 may be substantially rigid such that displacement portion 708 remains stationary relative to the humerus under the loads exerted by the deltoid muscle. Alternatively, spanning section 712 and/or displacement portion 708 may have some degree of flexibility so as to allow some movement of displacement portion 708 relative to the bone under certain loads. For example, spanning section 712 may have a flexibility selected such that if loads on displacement portion 708 exceed a preselected threshold, spanning section 712 will flex to allow displacement portion 708 to be deflected relative to the bone to which it is affixed.

The anterior edge 724 and the posterior edge 728 of the implant are also preferably convexly curved. In some embodiments, the proximal, anterior and posterior edges of the displacement section 708 are shaped to form a continuous arc similar to the lateral profile of the humeral head viewed in the sagittal plane. In some embodiments, the proximal, anterior and posterior edges of the displacement section 708 are shaped to form an arc viewed in the transverse plane. The inside surface 730 of the displacement portion 708 is preferably concave with a spoon-like shape to minimize contact with underlying soft tissue including lateral ligaments, the joint capsule, rotator cuff, etc. The cranial edge 732 of the spoon-like surface may also be shaped arcuately to minimize tissue irritation in general, and more specifically to avoid contact with the acromion during shoulder abduction. For example, the general dome shape of the displacement portion may curve down further along the cranial edge as shown so as to ride under the acromion as depicted in FIGS. 7G-I. In such an embodiment, the bearing surface may have a first curvature about an axis transverse to the humeral shaft, and the cranial edge of the displacement portion may curve inwardly/medially toward the humeral head about a second axis parallel to the first axis with a curvature having a second radius less than the first radius. In a further alternative to accommodate specific shoulder anatomy, the cranial edge also may be tapered in thickness to slide under the acromion, or alternatively shorter in the cranial direction or cut off on the cranial edge so it does not engage (is spaced laterally and/or caudally from) the acromion during arm abduction. This latter alternative may be accomplished, for example, by providing the dome-shaped displacement portion as a flattened side or concave area on the cranial edge in an area adjacent the cranial edge.

In one exemplary embodiment as shown, the fixation portion 704 is tapered from the cranial end to the caudal end. In other embodiments, the fixation portion 704 may have constant width. In the exemplary embodiment as shown, the width of the displacement portion 708 is substantially larger than the width of fixation portion 704, contributing to the overall spoon-like or paddle-like shape of implant 700.

The curvature and offset of the displacement portion 708 may be configured to displace the target tissue, e.g., the deltoid muscle laterally or antero-laterally. In one exemplary embodiment, the implant is placed on the lateral side of the humerus such that fixation portion 704 is substantially aligned with the humeral shaft, the spanning section 712 is in close apposition to a region of the humeral head, and the displacement portion 708 substantially covers or lies generally parallel to the humeral head. In some embodiments, the top view of the implant would mirror the lateral view of the proximal humerus, wherein the implant has a shaft region similar to the humeral shaft, an expanding neck region and a circular or oval or elliptical region similar to the coronal section of the humeral head.

In certain embodiments, implant 700 is configured to be rigid through the entire range of lateral loads such that the displacement portion of the implant remains substantially stationary relative to the humerus to which the implant is anchored. The rigidity of the implant could be altered by choice of material, increasing the thickness of the entire implant or increasing the thickness of certain regions of the implant. In another embodiment, the implant may be designed to provide some flexibility at the higher loads experienced during lifting, throwing, or pushing heavier loads. The flexibility of the implant could result in the displacement portion of the implant bending closer to the humeral head at higher loads. For example, an alternative exemplary implant is shown in FIG. 7F with two different possible thicknesses for spanning section 712. In this alternative embodiment, the implant is still anchored to the humerus through fixation portion 704 and displacement portion 708 is connected to the fixation portion through the spanning section 712. Spanning section 712 may be formed with relatively thicker and thinner parts (as shown at 741, 742), allowing the rigidity of the implant to be selected to provide the desired degree of deflection as it is subjected to a load due to the deltoid muscle crossing the displacement section 708. The thickness of the spanning section could be varied to have a rigid implant or a flexible compliant implant in the range of mechanical loads on the displacement portion. Similarly, the thickness of the entire implant could be varied to have a rigid implant or a flexible compliant implant.

In another embodiment, the elevated displacement portion 708 enables retaining the bursa and also avoids contact with the attachment of the rotator cuff to the humeral head. The bursa (shown in FIG. 3H) covers the attachment of the rotator cuff. FIGS. 7G and 7H show lateral and anterior views, respectively, illustrating positioning of implant 700 with the attachment region of the supraspinatus muscle (part of the rotator cuff) just cranial to displacement portion 708 when secured at a fixation site on the lateral, proximal humeral shaft as shown. Use of the space created between the humeral head and displacement portion 708 as a result of the elevated or cantilevered configuration of the implant may be best seen in the cross-sectional view of FIG. 7I. There it can be seen how this space accommodates a lateral/caudal-most portion of the Subdeltoid bursa. In exemplary embodiments, the size of the implant (as seen in the top view) would be proportionally smaller than the lateral profile of the proximal humerus, preferably about 5% to 25% smaller, or more preferably 10% to 20% smaller.

The implants described above may be implanted in areas adjacent to the joint such that the soft tissue is displaced in a region it crosses the joint. Alternatively, the device could be implanted further away from the joint and displace the target soft tissue in a region that it is not crossing the joint. For example, the device could be implanted proximally on the lateral humerus close to the humeral head to displace the deltoid muscle or the device could be implanted more distally along the humeral shaft where it displaces the deltoid muscle in a region away from the joint.

Figure 8:
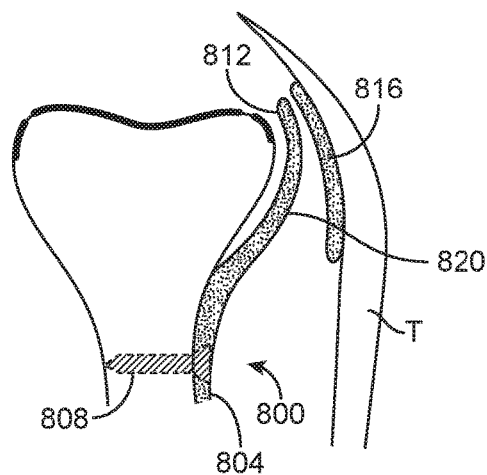
FIG. 8 is a view illustrating positioning of an alternative exemplary embodiment of the present invention at the cranial end of the humerus to treat the shoulder.

FIG. 8 depicts an alternative exemplary two-piece implant 800 according to an embodiment of the present invention wherein the two pieces are independent of each other and articulate over each other during joint motion. Fixation portion 804 of implant 800 is the fixed section of the implant and is attached to the bone with screw or screws 808. Displacement portion 812 includes a mobile bearing member 816 that bears upon fixed surface 820 of displacement portion 812. With this configuration, mobile bearing member 816 may be attached to the target soft tissue T. Either fixation portion 804 or displacement portion 812, or both may have a shape and size selected to displace mobile bearing 816, and thus tissue T, the desired degree. The two-piece design enables articulation between the surfaces of displacement portion 812 and mobile bearing 816; and reduces the risk of tissue wear due to motion of soft tissue over the implant surface. Mobile bearing member 816 may be attached to the soft tissue using sutures, adhesives, pins, wires, bands, etc., or otherwise as described above, including having the surface in contact with the soft tissue modified to enable tissue integration. The articulating surfaces between parts 812 and 816 also may have features like grooves to enable one surface to track a fixed path during flexion. The surfaces could be coated to minimize friction and wear. In some embodiments, the mobile section is attached to or embedded in the deltoid muscle. In other embodiments, the mobile section may be attached or embedded into the tendon or any other soft tissue surrounding the target joint. In some embodiments, bearing member 816 may comprise a soft, flexible, polymer membrane which can conform to the soft tissue and prevent contact between the soft tissue and the implant surface 820. In other embodiments, bearing member 816 may be inflatable, or include a capsule as previously described.

Figure 9:
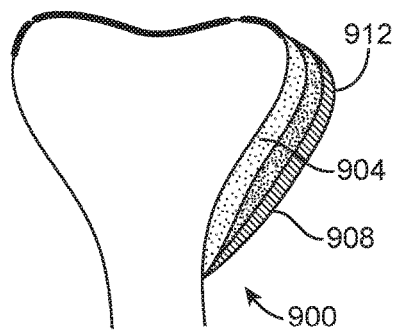
FIG. 9 is a view illustrating positioning of an alternative exemplary embodiment of the present invention at the cranial end of the humerus to treat the shoulder.
Figure 10:
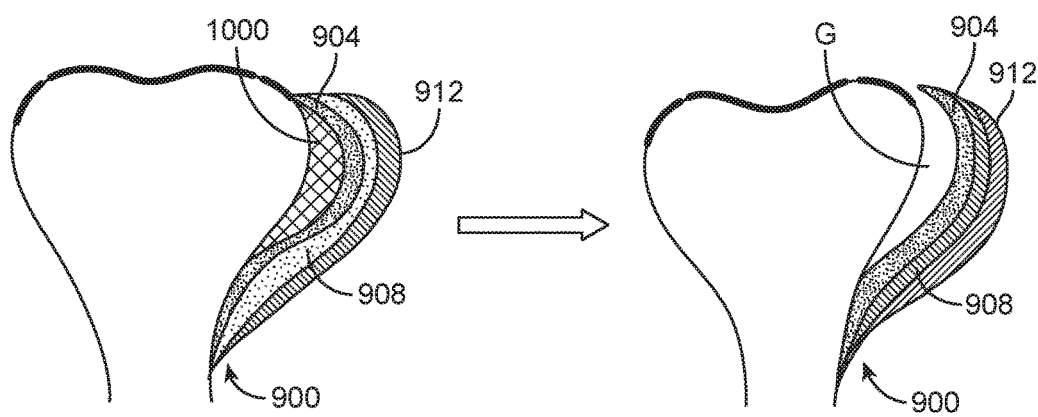
FIG. 10 is a view illustrating positioning of an alternative exemplary embodiment of the present invention at the cranial end of the humerus to treat the shoulder.

In further alternative embodiments, implants may also be fabricated in-situ by layering a polymerizing material on the underlying tissue such as in the embodiments of FIGS. 9 and 10. In such an embodiment, an implant could be contoured as needed by varying the material being layered in different regions of the implant. Removable molds or forms may be placed through an incision to the desired location against the bone to facilitate containment and shaping of the material prior to solidifying. In one exemplary shown in FIG. 9, implant 900 includes layers 904, 908 and 912, layered on top of each other to achieve the necessary displacement. The materials and the properties of each of the layers could be identical or different. For example, layer 904 may have adhesive properties to attach to the underlying bone, layer 908 may have high compressive strength to withstand the compressive load of the overlying soft tissue and layer 912 may have a smooth hydrophilic surface to minimize friction between the implant and the soft tissue during flexion/extension. In this example, layer 904 provides the fixation portion and layer 912 the displacement portion with layer 908 forming a spanning section therebetween. Adhesives may be used between the various layers. The materials could be polymerized in-situ using chemical crosslinkers, photo-initiated crosslinkers, thermally initiated crosslinkers, etc. The thicknesses of the various layers could be altered to achieve the necessary level of tissue displacement.

In an alternative exemplary embodiment of an in situ fabricated implant, as shown in FIG. 10, a spacer 1000 may be used to assist in fabricating the implant. The spacer 1000 could potentially be removed after the implant has been fabricated or may dissolve after the implant is installed, leaving behind a gap (G) between section 904 and the underlying soft tissue and bone. However, the implant and/or spacer may be designed to rest permanently on the underlying soft tissue and bone.

Figure 11:
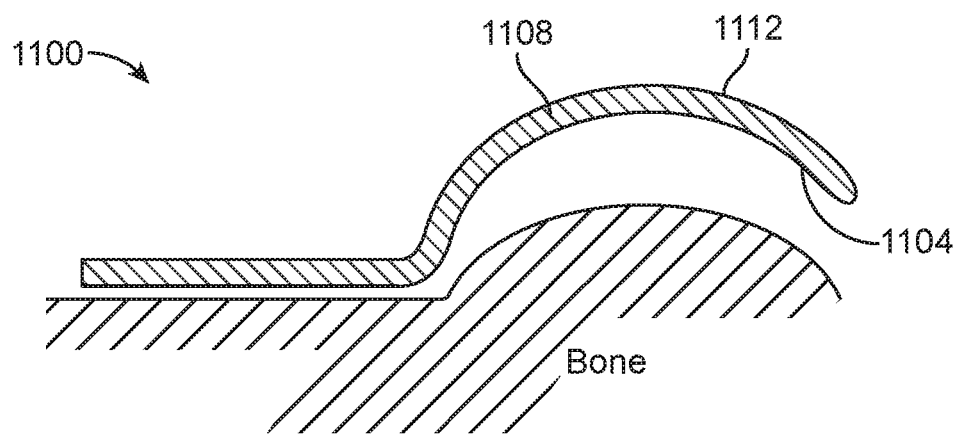
FIGS. 11-25 are partial cross-sectional views of the end the humerus adjacent the shoulder illustrating alternative exemplary embodiments of the present invention.

In some embodiments, the inferior surface of the displacement portion is elevated off the underlying tissue. The underlying tissue could be bone or soft tissue like tendon, muscle, ligament, bursa, capsule, etc. FIG. 11 depicts an implant 1100 with the inferior surface 1104 of the displacement section 1108 elevated off the underlying tissue. Elevating the inferior surface off the underlying tissue could be beneficial by minimizing interference with or damage to soft tissue, reducing any potential restriction to joint motion due to compression of soft tissue, etc.

In some embodiments, the displacement region will have a continuous bearing surface which is in contact with the target connective tissue (muscle, tendon, ligament, etc.) and is devoid of any discontinuities. Such discontinuities are usually undesirable as they create voids and interruptions in the smooth bearing surface, may have sharp edges or transitions, and may cause wear or abrasion of the displaced target tissue. Discontinuities would include fixation channels for long-term fixation like screw holes, holes for sutures, etc., as well as fixation channels for temporary fixation like holes for Kirschner-wires (K-wires).

FIG. 11 depicts an implant 1100 with a displacement section 1108 with a superior bearing surface 1112 and an inferior surface 1104. Displacement section 1108 is free of discontinuities in the bearing surface, such as holes that extend from the superior bearing surface 1112 to the inferior surface 1104 or those that extend from the superior bearing surface 1112 part way to the inferior surface 1104. The lack of discontinuities in the bearing surface minimizes the potential for wear or irritation of the target connective tissue. The bearing surface of the displacement section may be polished, coated, covered, or modified in other ways to minimize wear of the bearing surface and/or wear of the target connective tissue.

In some embodiments, the bearing surface of the displacement region which is in contact with the target connective tissue (muscle, tendon, ligament, etc.) may have features that enable adhesion or attachment of the target connective tissue to the bearing surface. Attachment of the target connective tissue on the implant surface may minimize motion of the tissue across the implant surface during joint motion. These features would include channels for formation of fibrous tissue from the target connective tissue anchoring the connective tissue to the displacement surface of the implant.

Figure 12:
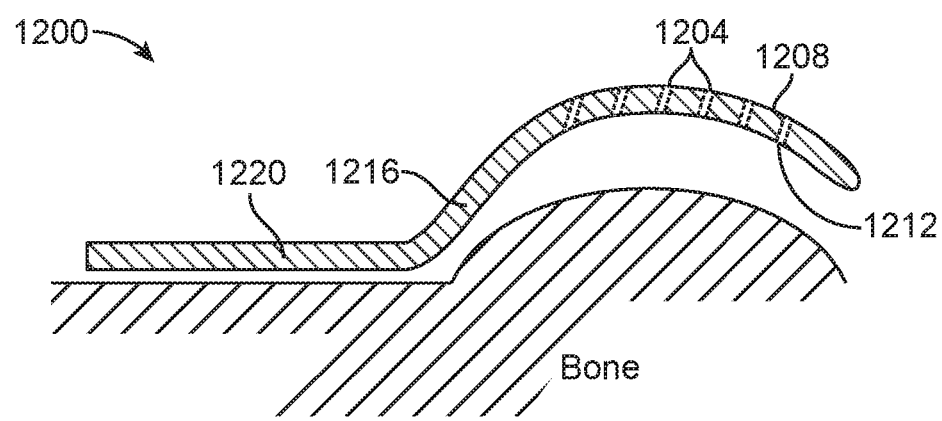
Figure 13:
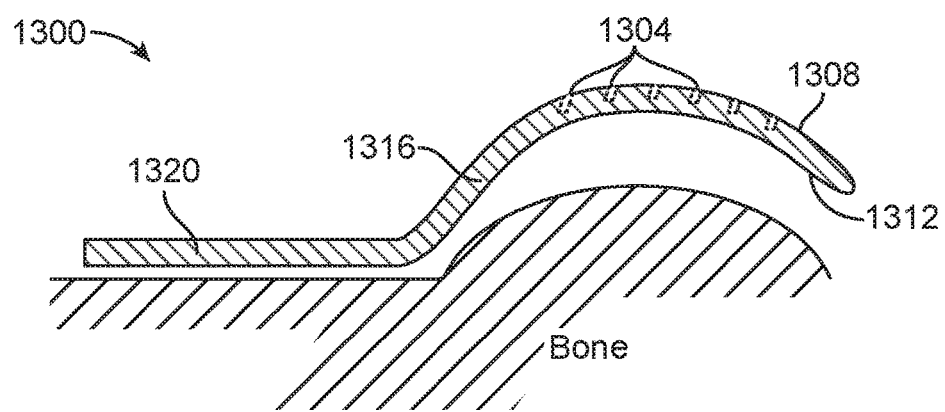

FIG. 12 depicts an implant 1200 with channels 1204 that extend from the superior bearing surface 1208 to the inferior surface 1212. FIG. 13 depicts an implant 1300 with channels 1304 extending from the superior bearing surface 1308 part way to the inferior surface 1312. The channels 1204 and 1304 may have varying cross-sectional shapes, e.g., square, circle, rectangle, oval, etc., with the largest cross-sectional dimension (for example, diameter of the circle, diagonal of a square or rectangle, major diameter of an oval, etc.) and will be dimensioned to promote adhesion and ingrowth of the target tissue, usually ranging from less than 1 mm to about 5 mm. In most cases such holes or channels will be substantially smaller than the fixation holes used in the fixation portion to accommodate bone screws or other fixation elements, typically having a diameter or width less than 50% and preferably less than 25% that of the fixation holes. The channels may be located across the entire bearing surface or across part of the bearing surface. In some embodiments, the displacement region may have one channel. In some embodiments, the displacement region may have two channels. In some embodiments, the displacement region may have three channels. In some embodiments, the displacement region may have more than three channels. In some embodiments, the channels may vary in depth across the bearing surface. The dimensions and cross-sectional shape of the channels across the displacement region may be identical or different. In some embodiments, the spanning section (e.g., 1216 and 1316) and/or the fixation section (e.g., 1220 and 1320) may also have similar features for attachment of the target connective tissue. In some embodiments, a region of the displacement section may have features for attachment of target connective tissue.

Figure 14:
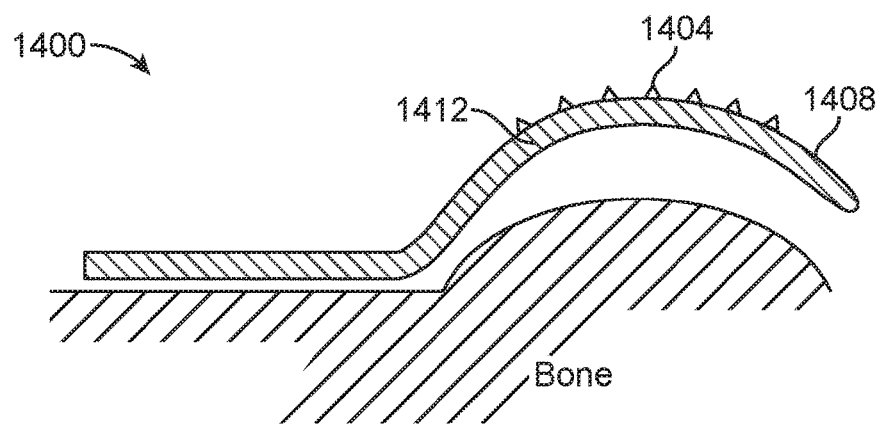
Figure 15:
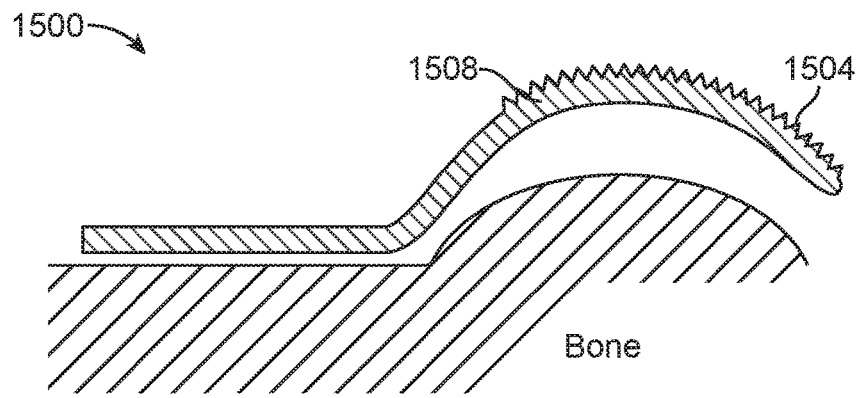
Figure 16:
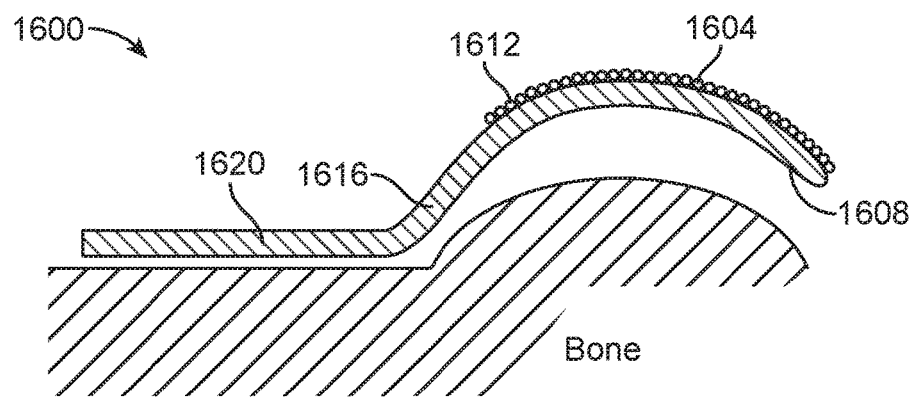

FIG. 14 depicts an implant 1400 with projections 1404 on the superior surface 1408 of the displacement section 1412. FIG. 15 depicts an implant 1500 with ridges on the superior surface 1504 of the displacement section 1508. FIG. 16 depicts an implant 1600 with a porous or granular surface 1604 on the superior surface 1608 of the displacement section 1612. In some embodiments, the spanning section (e.g., 1616) and/or the fixation section (e.g., 1620) may also have similar features for attachment of the target connective tissue. In some embodiments, a region of the displacement section may have features for attachment of target connective tissue.

Figure 17:
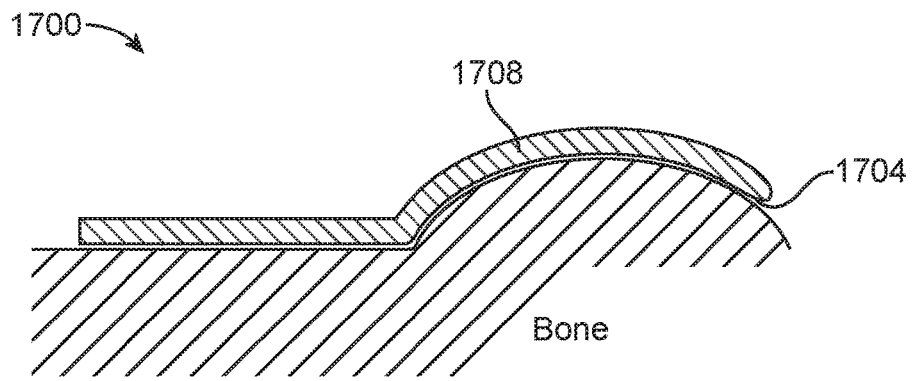

In some embodiments, the inferior surface of the displacement region may be in contact with the underlying tissue. FIG. 17 depicts an implant 1700 with the inferior surface 1704 of the displacement section 1708 in contact with the underlying tissue. In other embodiments, part of the inferior surface of the displacement section may be in contact with the underlying tissue.

In some embodiments, the inferior region of the displacement portion, spanning portion, or fixation portion may have features like channels for fibrous or bony tissue ingrowth to enable adhesion or attachment of the underlying tissue to the bearing surface. In other embodiments, the inferior region may have features like projections, microprojections, bumps, ridges, pin-like projections, granular surface, etc. Attachment of any soft connective tissue underneath the inferior surface of the displacement region may minimize motion of the tissue under the implant during joint motion. In other embodiments, the inferior surface may have pins for anchoring the implanting into underlying bone.

Figure 18:
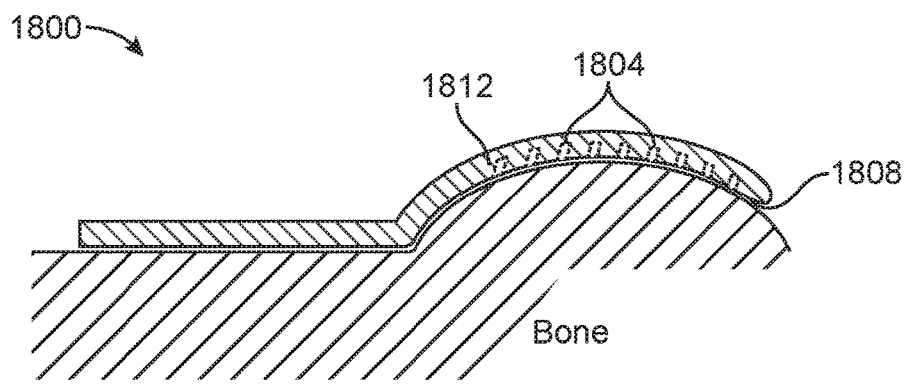

FIG. 18 depicts an implant 1800 with holes or channels 1804 in the inferior portion 1808 of the displacement section 1812. The holes or channels 1804 may have varying cross-sectional shapes, e.g., square, circle, rectangle, oval, etc., with the largest cross-sectional dimension (for example, diameter of the circle, diagonal of a square or rectangle, major diameter of an oval, etc.) ranging from less than 1 mm to about 5 mm. The holes or channels may be distributed across the entire inferior surface or across part of the inferior surface of the displacement section. The holes or channels may extend entirely through the thickness of displacement section 1812, but in preferred embodiments extend only partially through the thickness (e.g., in blind holes or channels) such that the outward-facing bearing surface of displacement section 1812 is continuously smooth and uninterrupted by such holes, channels, or other discontinuities.

Figure 19:
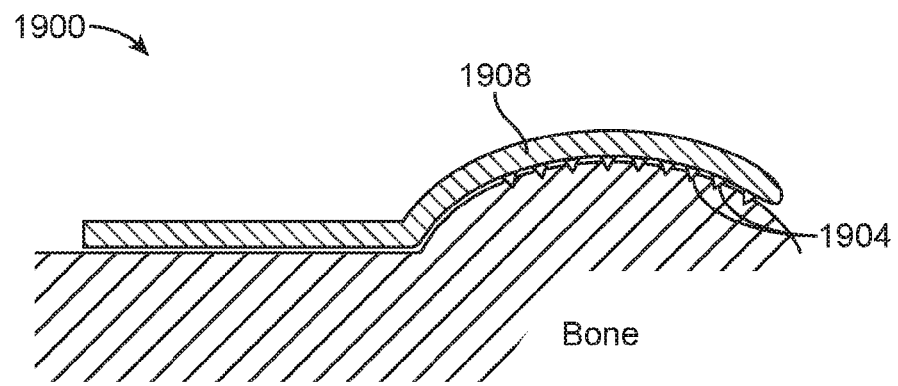
Figure 20:
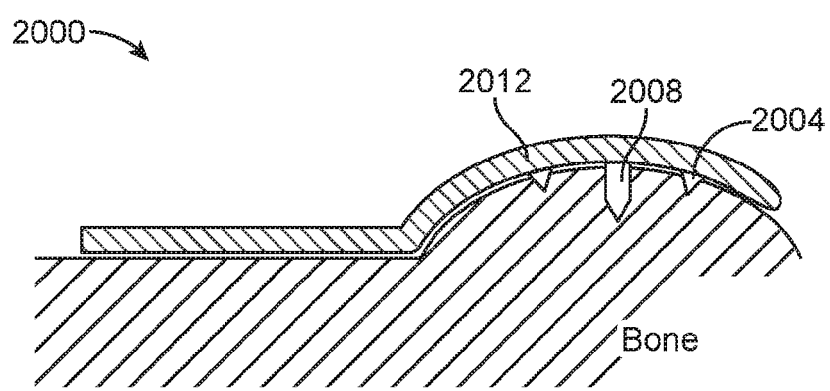

FIG. 19 depicts an implant 1900 with projections 1904 from an inferior surface of the displacement section 1908. FIG. 20 depicts an implant 2000 with pins 2004 and 2008 from the inferior surface of the displacement section 2012. Such projections or pins may encourage tissue adhesion as well as stabilize the displacement portion and restrain it from motion relative to the underlying bone.

In some embodiments, the device may be a two-part device with the first part (base unit) comprising the fixation section, the displacement section (and optionally, the spanning section), and the second part (bearing unit) configured to attach to the displacement section of the base unit. In other embodiments the bearing unit may be configured to attach to the spanning section and to cover the displacement section of the base unit. The bearing unit may be configured to minimize tissue wear or to enable tissue adhesion or attachment. In one embodiment, the displacement section and the bearing unit would have features to attach the two units.

Figure 21:
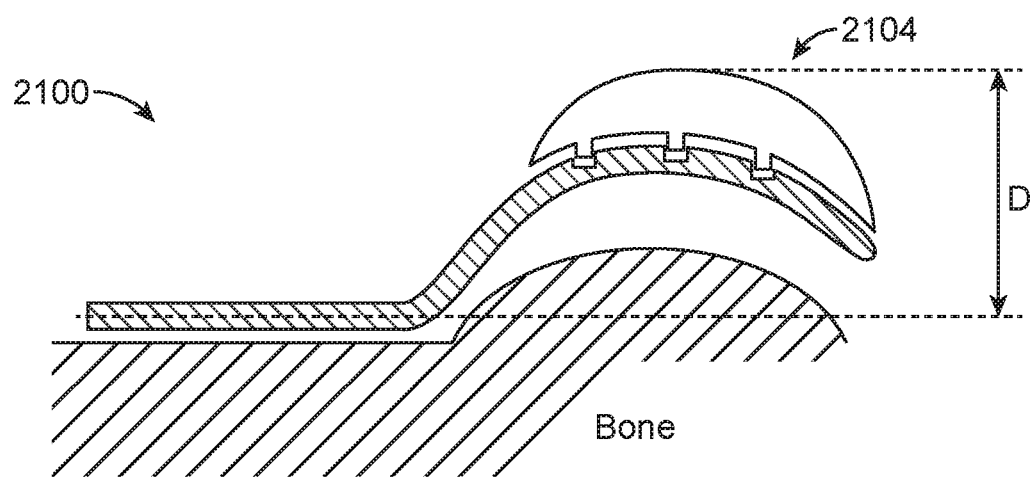
Figure 22:
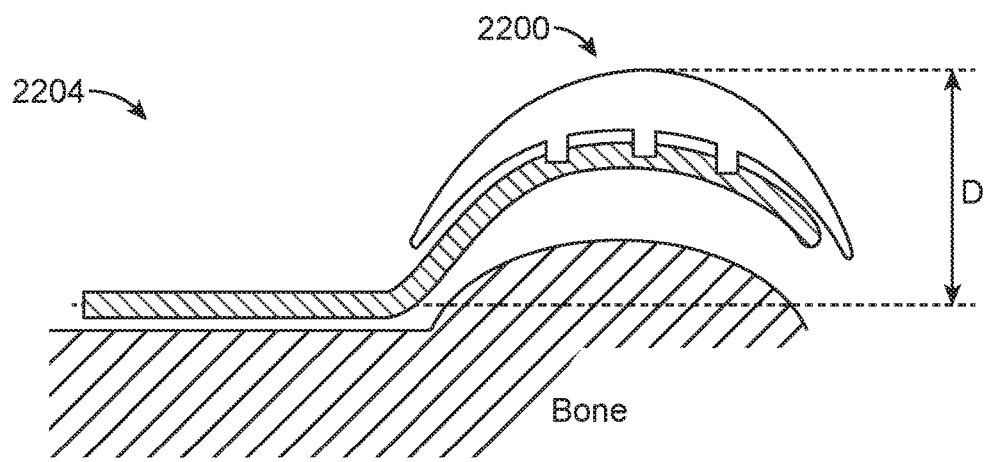
Figure 23:
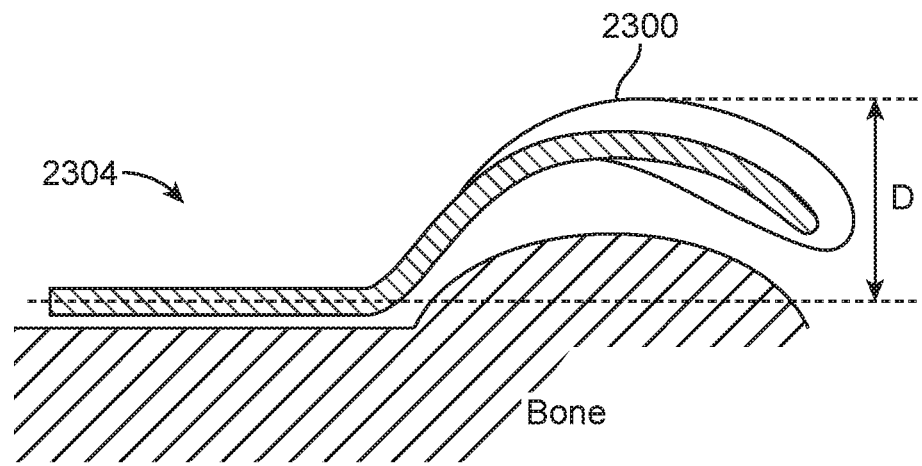
Figures 26A, 26B:
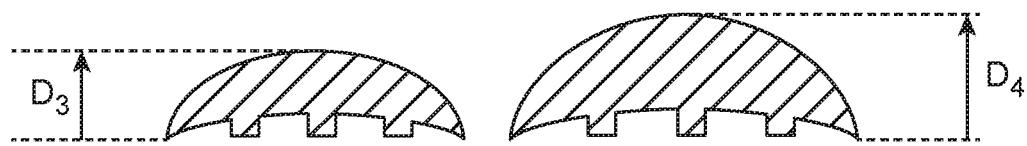
FIGS. 26A-B are exemplary embodiments of the bearing unit of a two-part device.
Figure 27:
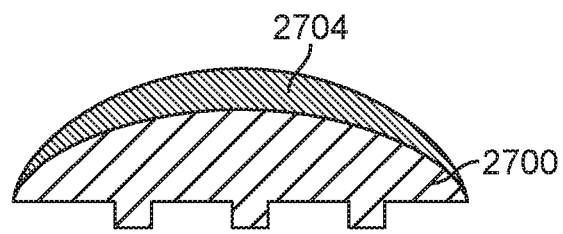
FIG. 27 is an exemplary embodiment of a composite bearing unit of a two-part device.

FIG. 21 depicts an exemplary two-part implant with a base unit 2100 and a bearing unit 2104. FIG. 23 depicts another exemplary embodiment of a two-part implant with a bearing unit 2300 slipped over the displacement section of the base unit 2304 so as to cover the superior surface, the cranial end, and at least a portion of the inferior surface of the displacement section. Attachment of the bearing unit would increase the depth of the composite implant D (FIGS. 21, 22, and 23). To alter the depth of the composite implant, bearing units of different dimensions $D_3$ and $D_4$ (FIGS. 26A-B) may be attached intra-operatively to a base unit before it is anchored to the target site or to a base unit that has been anchored to the target site on the humerus to obtain the necessary target connective tissue displacement. In some embodiments, the bearing unit may cover the entire displacement section of the base unit. In other embodiments, the bearing unit may cover part of the displacement region. In some embodiments, the bearing unit 2200 may extend beyond the displacement section of the base unit 2204 (FIG. 22). The bearing unit may be rigid or may comprise a rigid base 2700 with a compliant surface 2704 (FIG. 27).

Figure 24:
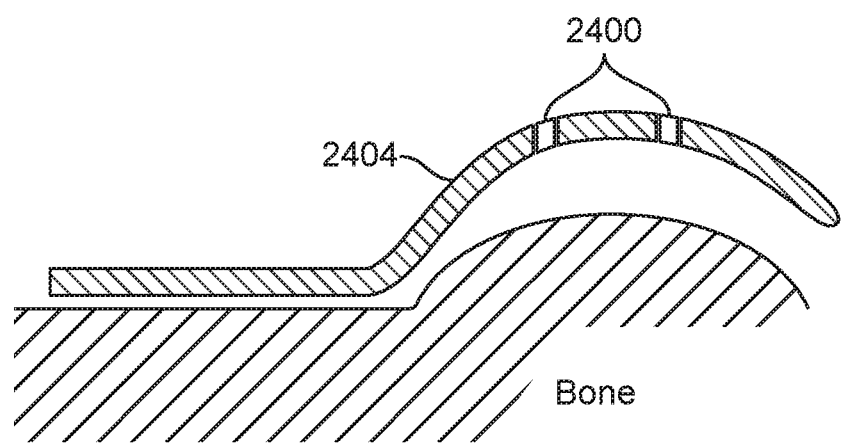
Figure 25:
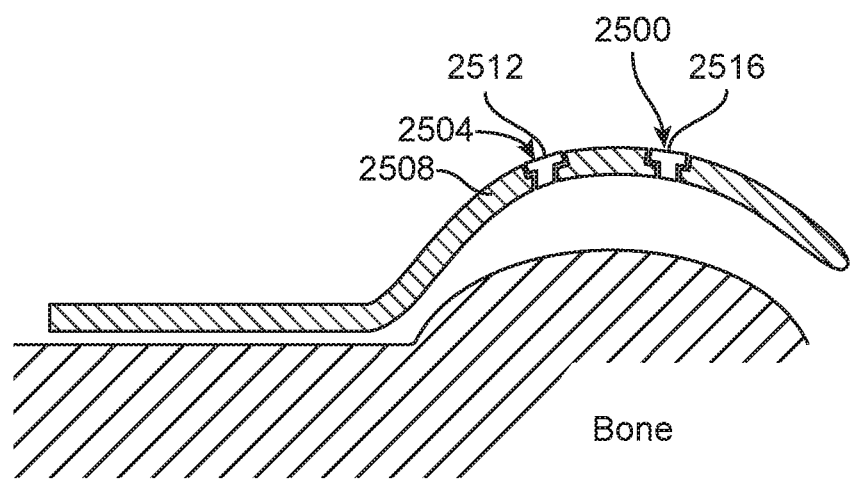

In some embodiments, the displacement region may have channels to assist in positioning, placement or temporarily anchoring of the implant intra-operatively. FIG. 24 depicts an implant with channels 2400 in the displacement section 2404 to assist in positioning of the implant during a percutaneous or minimally invasive surgery. FIG. 25 depicts an implant with channels 2500 and 2504 in the displacement section 2508 to assist in positioning of the implant during a percutaneous or minimally invasive surgery. The channels in the implants shown in FIGS. 24 and 25 may be covered with caps (e.g., 2512, 2516) configured to fit into the channels to render the bearing surface of the displacement region completely smooth and substantially devoid of any discontinuities.

As will be evident to one skilled in the art, the dimensions of the exemplary embodiments above can be altered to address differences in joint size, level of the tissue displacement, etc., as well as to enable positioning and securing the implant at the surgical site while minimizing trauma to the surrounding bone, tendons, muscles, ligaments and other anatomical structures.

A further aspect of the present invention includes methods for treating the shoulder, including reducing pain and/or increasing stability by implanting prostheses as described herein. One exemplary method thus comprises selecting at least one of the associated muscle and connective tissues surrounding a joint as target tissue for treatment, displacing the target tissue without severing the bones or target tissue, and altering the kinematics of the joint thereby. In a further embodiment, altering the kinematics of the joint achieves a therapeutic effect as described herein. In other embodiments, altering the kinematics of the joint redistributes loading in the joint and/or reduces loading on the ligaments within the joint and/or tendons adjacent the joint (e.g., rotator cuff or portions thereof). In some embodiments prostheses according to the present invention may be placed with therapeutic effect without rupturing the joint capsule and without any portion of the implant entering the joint capsule. In addition, the implants of the invention may be implanted without cutting, removing, or reshaping any bones, other than drilling holes to receive fixation screws or other devices.

In general, methods of treatment in accordance with the present disclosure will involve a pretreatment assessment of the joint and conditions to be addressed, for example, alterations in loading, pain reduction, stability enhancement, or combinations of such symptoms. Assessment will allow the treating physician to determine the most appropriate fixation site on appropriate bones associated with the joint to be treated, which, in the case of the shoulder, will typically be the humerus, and in many situations, more specifically a site disposed on the lateral, proximal humeral shaft adjacent the humeral head. Assessment also will involve a determination of the target tissue to be treated and the amount the target tissue is to be displaced from its natural, anatomical path in order to achieve the desired therapeutic effect.

With such determinations made during an assessment phase, the prostheses may be specifically configured and dimensioned to address the anatomy of the joint to be treated for a particular patient. With respect to treatments of the shoulder, this will typically involve configuring a fixation portion of the implant specifically to be secured at a selected fixation point on the humeral surface and configuration of a displacement portion to insert under and engage the targeted tissue by an amount consistent with the needed displacement as determined in assessment. Configuration to properly position the displacement portion may also require a specific configuration of a spanning section as described herein in cooperation with the configuration of the displacement portion.

Once the prosthesis configuration is determined based on patient anatomy and pretreatment assessment, the appropriately configured and dimensioned prosthesis may be implanted following accepted, less invasive surgical techniques. Such a surgery would typically involve an appropriately placed entry incision to gain access to the fixation site, while avoiding rupture of the joint capsule or positioning of the implant that would cause it to penetrate into the capsule. Based on the unique configuration of prostheses as described herein, surgical implantation and treatment by displacement of targeted tissue is accomplished without cutting or repositioning the bones associated with the joint to be treated. In this context, as previously mentioned and consistent with the less invasive approach of the present invention, the comparatively minor intrusion into the bone by bone screws or similar fixation means to secure the implant at the fixation site is not considered a cutting of the bone.

Based on the configuration of the implant as described herein, the engagement with and displacement of the target tissue occurs concomitantly with placement and fixation of the implant at the fixation site. Once placement is confirmed, the surgical incision may be closed in accordance with standard orthopedic surgical practices. Post-operative physical therapy may be prescribed as appropriate, however it is anticipated that in most cases the therapeutic benefit of the prosthesis will be felt essentially immediately post-operatively or at least as soon as the initial surgical side effects of pain and swelling diminish.

In one embodiment, displacement of the target tissue results in the decrease in the mechanical load on targeted regions of the articular cartilage in the shoulder joint by at least 5%, more preferably by at least 8%, most preferably by at least 10%. Unloading as defined here refers to a decrease in contact forces, either peak forces or average forces, either measured or calculated, during physical activity that results in mechanical loading of articular cartilage in a joint.

While the invention has been illustrated by examples in various contexts, the devices of the present invention may be used to displace any of the muscles and connective tissues around the shoulder to achieve a therapeutic effect. Alternatively, the tendon associated with any of the muscles could be displaced. Also, while examples are discussed in contexts of treating human joints associated with force imbalances, it will be understood that the invention may also have application to treatment of focal defects caused by trauma or other reasons.

Alternatively, the devices and methods of the invention could be used in conjunction with other therapies used to treat focal and diffuse lesions on the humeral head. For example, the device for unloading a region of the humeral head could be used in conjunction with microfracture or autologous chondrocyte implantation (ACI) therapy of a focal cartilage lesion on the humeral head.

Other applications of devices and methods of the invention include use in conjunction with labral repair treatment (e.g., suture anchors) to reduce loading on the repaired labrum. For example, during the repair of the anterior glenoid labral tear (e.g., Bankart lesion), a device of the invention could be implanted surgically to anteriorly displace the biceps brachii long head. By increasing the moment arm of the biceps brachii tendon, the anterior stability of the shoulder could be increased. Alternatively, the load on the repaired glenoid labral may be reduced thereby reducing the risk of failure or re-tearing of the repaired labrum.

Devices and methods of the invention could be used in conjunction with rotator cuff repair treatment (sutures, tacks, suture anchors, patches, membranes, etc.). For example, during the repair of a rotator cuff tear using suture anchors, tissue patches, etc., a device of the invention could be implanted surgically to laterally displace the deltoid muscle. By increasing the moment arm of the deltoid muscle, the load of the rotator cuff may be reduced during shoulder abduction, thereby reducing the risk of failure or re-tearing of the repaired rotator cuff and/or reducing pain due to the mechanical strain on the rotator cuff tissue.

Alternatively, devices and methods of the invention could be used to treat rotator cuff injury, pain, tear, etc. For example, a device of the invention could be implanted surgically to laterally displace the deltoid muscle. By increasing the moment arm of the deltoid muscle and increasing its ability to support the movement of the shoulder joint, the load of the rotator cuff may be reduced during shoulder abduction, thereby reducing pain due to the mechanical strain on the rotator cuff. In a further alternative, another application is in use for treating shoulder laxity as an alternative or adjunct to capsular imbrication and thermal capsular shrinkage (capsulorrhaphy).

Another application includes use in conjunction with total shoulder replacement devices including reverse shoulder replacement devices to alter the mechanical forces on the new joint, thereby increasing the stability of the replaced joint and reducing the risk of implant wear. During surgery to replace the shoulder joint, implants of the present invention could be implanted on the proximal humerus to increase the moment arm of the surrounding soft tissue, and thereby, improve the mechanical impact of the surrounding tissue on shoulder stability.

While the implants of the present invention could be implanted simultaneously while performing another surgery (e.g., rotator cuff tear repair, shoulder replacement, etc.), the implant may also be surgically placed in a subsequent surgery. The implants of the present invention could be used as a permanent implant (for example, implant that survives in a patient for more than five years) or a temporary implant. In some instances, implants of the present invention may be used as a temporary adjunct to improve the outcome of another procedure. For example, the implant used in conjunction with an anterior labral tear repair may be removed once the repaired labrum has healed.

The invention may further be adapted to displace tissues acting on various other joints so as to reduce or otherwise alter loads therein, including the elbow, shoulder, wrist, fingers, spine, ankle, interphalangeal joints, jaw or other joints. For example, the implants of the invention may be configured for attachment to the acetabulum, vertebrae of the spine, scapula, humerus, radius, ulna, carpals, metacarpals, tarsals, metatarsals, talus or other bones of the foot, among other bones.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method for treating disorders of the shoulder, comprising mounting a prosthesis on the humerus at a fixation site to displace a target tissue comprising a connective tissue or muscle of the shoulder from a normal, anatomical path in at least one direction to alter loads applied by the connective tissue or muscle to the shoulder joint without cutting the humerus in said mounting or displacing, wherein said mounting and displacing are performed without rupturing a joint capsule of the shoulder or without the prosthesis entering any portion of the joint capsule.

2. The method of claim 1, wherein the target tissue is a deltoid muscle and said displacement is in a lateral or antero-lateral or postero-lateral direction.

3. The method of claim 2, wherein said mounting comprises mounting the implant cranially on the lateral side of the humeral shaft to displace the deltoid muscle around the humeral head.

4. The method of claim 1, wherein said displacing decreases mechanical load on at least one region of the articular cartilage of the shoulder by at least about 5%.

5. The method of claim 1, wherein the target tissue is a biceps brachii tendon and said displacement is in an anterior direction.

6. The method of claim 5, wherein said mounting comprises mounting the implant cranially on the humeral shaft to displace the biceps brachii tendon.

7. The method of claim 1, wherein said displacing decreases mechanical load on at least one of the rotator cuff tendons.

8. The method of claim 1, wherein said displacing increases the stability of the shoulder joint during shoulder motion.

9. The method of claim 1 wherein the implant avoids interference with an acromion during arm abduction.

10. The method of claim 9 wherein the implant slips under the acromion during arm abduction.

11. The method of claim 9 wherein the implant is spaced laterally and/or caudally from the acromion when the arm is abducted.

12. A method for treating disorders of the shoulder, comprising mounting a prosthesis on the humerus at a fixation site to displace a target tissue comprising a connective tissue or muscle of the shoulder from a normal, anatomical path in at least one direction to alter loads applied by the connective tissue or muscle to the shoulder joint without cutting the humerus in said mounting or displacing, wherein:
the prosthesis comprises a fixation portion and a displacement portion separated and connected by a spanning section;
said mounting comprises securing the fixation portion to a fixation site on the proximal humeral shaft without rupturing the shoulder joint capsule; and
said displacing comprises positioning the displacement portion under and in engagement with the target tissue with the fixation portion secured at the fixation site.

13. The method of claim 12, wherein said displacing comprises displacing the target tissue from its natural, anatomical path to a therapeutic path by a distance from greater than about 5 mm to about 30 mm.

14. The method of claim 12, wherein said mounting and displacing are performed without rupturing a joint capsule of the shoulder or without the prosthesis entering any portion of the joint capsule.

* * * * *